US012646591B2

(12) United States Patent
Packer et al.

(10) Patent No.: US 12,646,591 B2
(45) Date of Patent: Jun. 2, 2026

(54) SYSTEMS AND METHODS FOR REDUCING MEMORY PROCESSING RESOURCES FOR DETECTING INTERACTIONS OF ALTERNATES

(71) Applicant: Foresite Labs, LLC, San Francisco, CA (US)

(72) Inventors: Jonathan S. Packer, San Francisco, CA (US); Connor Emdin, San Francisco, CA (US); Frederick Dewey, San Francisco, CA (US); Mary Helen Black, San Francisco, CA (US)

(73) Assignee: Foresite Labs, LLC, San Francisco, CA (US)

( * ) Notice: Subject to any disclaimer, the term of this patent is extended or adjusted under 35 U.S.C. 154(b) by 0 days.

(21) Appl. No.: 18/952,988

(22) Filed: Nov. 19, 2024

(65) Prior Publication Data

US 2026/0141984 A1 May 21, 2026

Related U.S. Application Data

(63) Continuation of application No. PCT/US2023/079695, filed on Nov. 14, 2023.

(60) Provisional application No. 63/425,579, filed on Nov. 15, 2022.

(51) Int. Cl.
| | |
|---|---|
| *G01N 33/48* | (2006.01) |
| *G01N 33/50* | (2006.01) |
| *G16B 40/30* | (2019.01) |
| *G16B 50/30* | (2019.01) |
| *G16C 20/50* | (2019.01) |

(52) U.S. Cl.
CPC ............. *G16B 40/30* (2019.02); *G16B 50/30* (2019.02); *G16C 20/50* (2019.02)

(58) Field of Classification Search
CPC ......... G16B 40/30; G16B 50/30; G16C 20/50
See application file for complete search history.

(56) References Cited

U.S. PATENT DOCUMENTS

2013/0073217 A1* 3/2013 Dewey .................. G16B 40/30
702/20

OTHER PUBLICATIONS

Golub et al. Molecular classification of cancer: Class discovery and class prediction by gene expression monitoring. Science, vol. 286, pp. 531-537. (Year: 1999).*
Vrabie et al. Independent component analysis of Raman spectra: Application of paraffin-embedded skin biopsies. Biomedical Signal Processing and Control, vol. 2, pp. 40-50. (Year: 2007).*

(Continued)

*Primary Examiner* — Russell S Negin
(74) *Attorney, Agent, or Firm* — Foley & Lardner LLP

(57) ABSTRACT

A system for reducing memory processing resources comprises one or more processors configured to generate a plurality of principal components (PCs) corresponding to characteristic data for entities in a dataset to reduce a size of the dataset; generate a score for each entity in the dataset based at least on (i) the PCs, and (ii) weights for a condition of interest; determine a set of alternates that correspond to the condition of interest; determine, using a machine learning model, interactions between the set of alternates for one or more target components corresponding to the object and the scores, wherein the interactions are indicative of a response for the condition of interest; and perform one or more actions.

20 Claims, 7 Drawing Sheets

(56)                References Cited

OTHER PUBLICATIONS

Zhong et al. Investigation and analysis of single nucleotide polymorphisms in Janus kinase/signal transducer and activator of transcription genes with leukemia. Leukemia & Lymphoma, vol. 53, pp. 1216-1221. (Year: 2012).*

International Search Report and Written Opinion from PCT/US2023/079695, dated May 8, 2024.

Johnson Danielle et al., A systematic review and analysis of the use of polygenic scores in pharmacogenomics, Clinical Pharmacology and Therapeutics, vol. 111, No. 4, Jan. 17, 2022, pp. 919-930.

Siemens Angela et al., A systematic review of polygenic models for predicting drug outcomes, Journal of Personalized Medicine, vol. 12, No. 9, Aug. 27, 2022, p. 1394.

Zhai Song et al., Pharmacogenomics polygenic risk score for drug response prediction using PRS-PGx methods, Nature Communications, vol. 13, No. 1, Sep. 8, 2022.

* cited by examiner

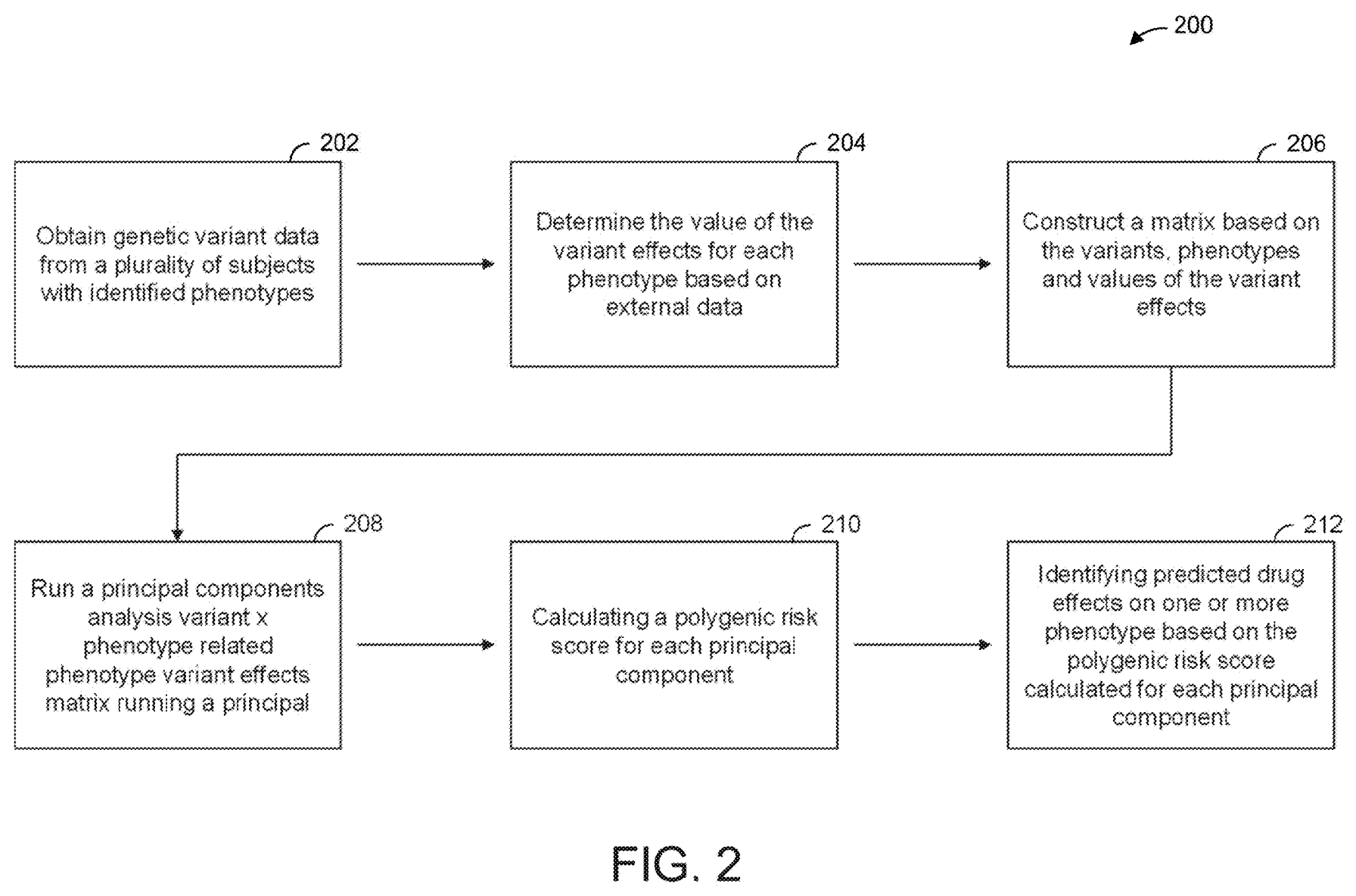

200

202

Obtain genetic variant data from a plurality of subjects with identified phenotypes

204

Determine the value of the variant effects for each phenotype based on external data

206

Construct a matrix based on the variants, phenotypes and values of the variant effects

208

Run a principal components analysis variant x phenotype related phenotype variant effects matrix running a principal

210

Calculating a polygenic risk score for each principal component

212

Identifying predicted drug effects on one or more phenotype based on the polygenic risk score calculated for each principal component

FIG. 2

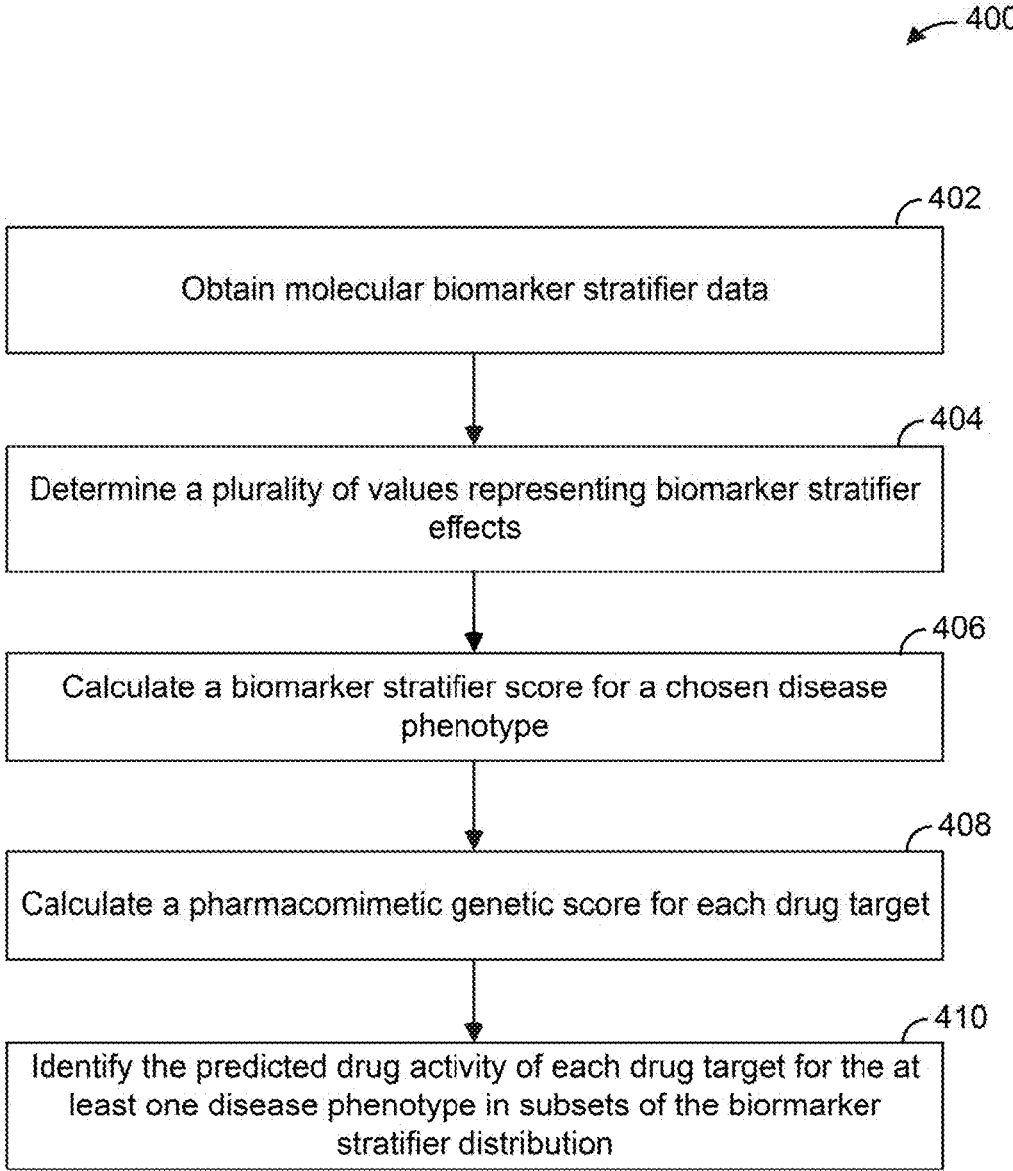

400

402

Obtain molecular biomarker stratifier data

404

Determine a plurality of values representing biomarker stratifier effects

406

Calculate a biomarker stratifier score for a chosen disease phenotype

408

Calculate a pharmacomimetic genetic score for each drug target

410

Identify the predicted drug activity of each drug target for the at least one disease phenotype in subsets of the biormarker stratifier distribution

FIG. 4

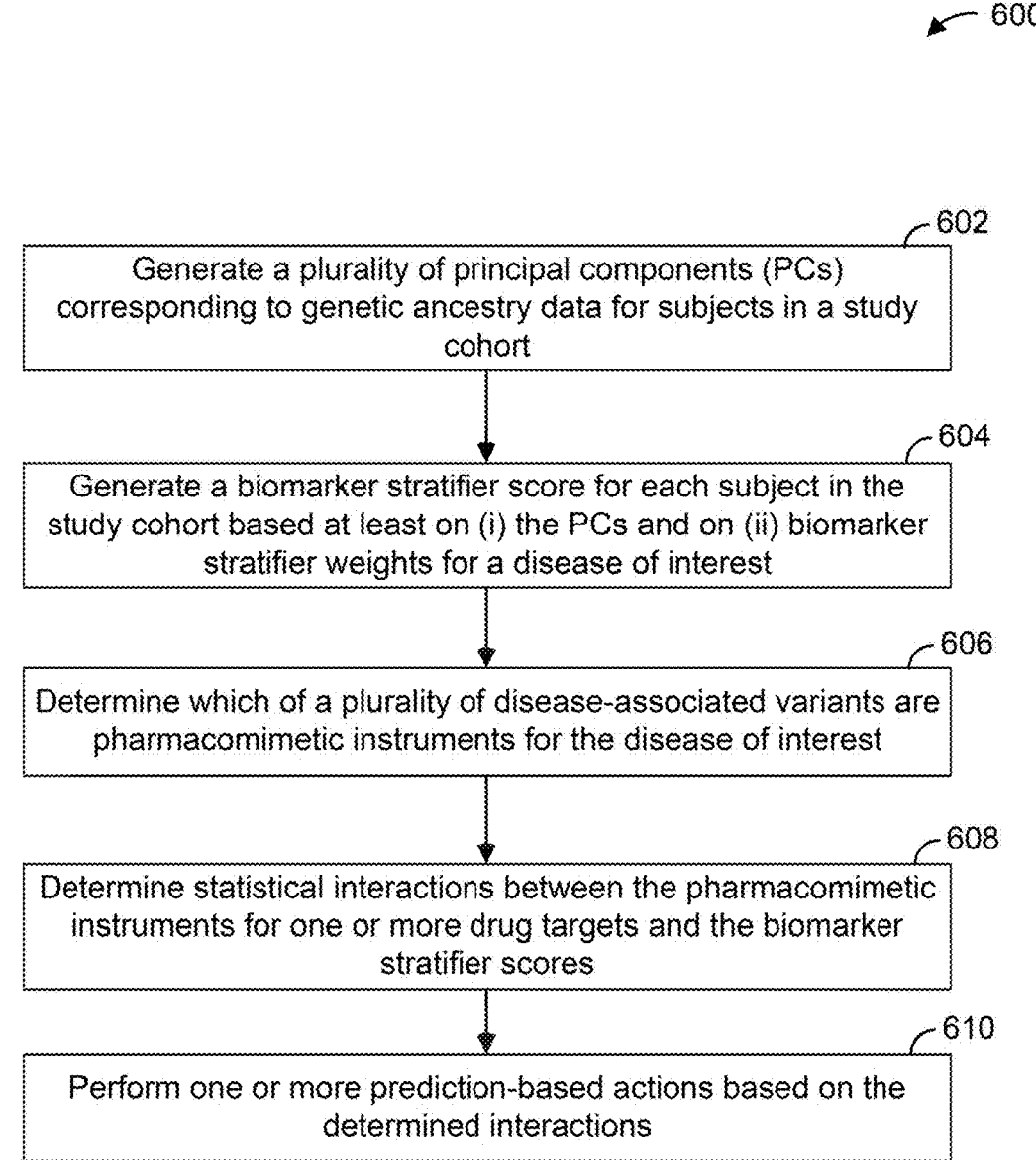

600

602
Generate a plurality of principal components (PCs) corresponding to genetic ancestry data for subjects in a study cohort 604
Generate a biomarker stratifier score for each subject in the study cohort based at least on (i) the PCs and on (ii) biomarker stratifier weights for a disease of interest 606
Determine which of a plurality of disease-associated variants are pharmacomimetic instruments for the disease of interest 608
Determine statistical interactions between the pharmacomimetic instruments for one or more drug targets and the biomarker stratifier scores 610
Perform one or more prediction-based actions based on the determined interactions

FIG. 6

SYSTEMS AND METHODS FOR REDUCING MEMORY PROCESSING RESOURCES FOR DETECTING INTERACTIONS OF ALTERNATES

CROSS-REFERENCE TO RELATED APPLICATIONS

This application claims the benefit of priority as a bypass continuation of PCT Application No. PCT/US2023/079695, filed Nov. 14, 2023, which claims the benefit of priority to U.S. Provisional Application No. 63/425,579, filed Nov. 15, 2022.

FIELD OF THE DISCLOSURE

The present disclosure relates to systems, methods and computer program products for drug development using in silico techniques.

BACKGROUND OF THE DISCLOSURE

Modelling and simulation are rapidly evolving areas in terms of both technologies and application fields in the life sciences. The use of modeling and simulation has expanded beyond the description of drug exposure, towards the dynamic description of complex drug effects and disease subtypes and progressions. In recent years, new approaches in modelling and simulation have started to provide important insights in biomedicine, opening the way for their potential use in the reduction, refinement and partial substitution of both animal and human experimentation.

SUMMARY OF ILLUSTRATIVE EMBODIMENTS

Polygenic scores (PGS), herein used interchangeably with polygenic risk scores (PRS), summarize genome-wide genotype data in combination with gene-phenotype association data, such as from genome-wide association studies (GWAS), into metrics that represent genetic liability to a trait. The present disclosure provides in silico systems, methods and computer program products using PRS for various aspects of drug development and optimization of patient treatment, including drug indication selection and clinical trial recapitulation. Specifically, the disclosure provides PRS-informed drug development systems to accelerate the development of new therapeutic products as well as repurposing existing therapies for new populations and/or indications. There are many applications of PRS-informed drug development, ranging from discovery of new drug targets for the treatment of a given indication, to repurposing of existing therapeutics for new indications, to new and efficient designs of clinical trials, to incorporation of new end points in ongoing clinical trials, to modifying how the data are analyzed to provide evidence of effectiveness in powering clinical trials, to modifying how existing therapeutics are used in patient populations. These systems utilize existing patient variant data in conjunction with computational models to mimic aspects of the drug development process. Importantly, the systems of the disclosed approach allow such development without the requirement of empirical data that has to date been required for various steps in the drug development process, from drug discovery through clinical trials and regulatory approval, although empirical data is optionally incorporated in certain embodiments.

In addition to the patient variant data, the computational models of the systems of the disclosure can optionally use mechanistic knowledge of physical, chemical, and/or environmental data related to patient populations and available biological and physiological knowledge of patient treatment (such as medical intervention) or activity (such as exercise or lack thereof).

In some aspects, the disclosure provides a preclinical drug discovery system for identifying and/or developing treatments (e.g., drugs) for various therapeutic areas and indications. The preclinical drug discovery system is configured to utilize mammalian polygenic scores with computational models to provide PRS-informed drug discovery methodologies. Potential uses of such methods are set forth on FIG. 1.

In some aspects, the disclosure provides a drug discovery system for repurposing existing therapeutics for new therapeutic areas and indications. The system is configured to utilize mammalian polygenic scores with computational models to provide PRS-informed methodologies with known drug and patient information to find potential new uses of existing therapies.

In some embodiments, the disclosure provides in silico systems and methods for determining drug activity. In particular, the disclosure provides systems and methods for determining drug activity for particular patient populations, phenotypes, or for use in therapeutic indications/areas. This drug activity may be determined for known agents or for de novo agents.

Accordingly, in some aspects, the disclosure provides an in silico method for determining drug activity of drug targets on a plurality of phenotype intermediates, comprising, or alternatively consisting essentially of, or yet further consisting of obtaining data on genetic variants and phenotypes from each of a plurality of subjects, determining the value of the variant effects for each phenotype intermediate based on external data, calculating a polygenic score for each phenotype intermediate in the disease process, calculating a pharmacomimetic genetic score for each drug target on each phenotype intermediate, and identifying predicted drug activity of the drug targets on one or more phenotypes based on the statistical interaction of the polygenic score with the pharmacomimetic genetic score for each drug target in association analysis with the phenotype intermediate and the outcome phenotype. In some aspects, the disclosure provides a system for providing in silico clinical trials for new therapeutics using mammalian polygenic scores with computational models. Historically, safety and efficacy data provided to regulatory agencies in support of marketing authorization of a new medical product have been produced experimentally, either in vitro or in vivo. More recently, regulatory agencies started receiving and accepting in silico data produced using modelling and simulation, and the data provided by the systems of the disclosure can provide data supporting regulatory filings without the need for expensive and time-consuming experimentation.

The systems of the disclosure allow development of patient-specific models to form virtual cohorts for testing the safety and/or efficacy of new drugs and of new medical devices.

In certain embodiments, the disclosure provides in silico methods for determining drug activity, the methods comprising, or alternatively consisting essentially of, or yet further consisting of obtaining data on genetic variants and phenotypes from each of a plurality of subjects; determining the value of each variants' effect on each phenotype based on external data from a non-overlapping set of subjects;

constructing a matrix in which the variants are rows, the phenotypes are columns, and the values are the externally-derived variant effects; running a truncated principal components analysis on this matrix, computing a user-defined number of principal components, typically two to five; calculating a polygenic score for each computed principal component by reweighting an existing polygenic score for a user-defined "reference" phenotype such that the new weight for each variant included the polygenic score is equal to its old weight times its squared loading for the principal component in question divided by the sum of its squared loadings across all computed principal components; and lastly identifying predicted drug activity for the "reference" phenotype based on each of the reweighted polygenic scores, which often can be interpreted as corresponding to biological pathways. This example method is set forth visually in FIG. 2.

In certain embodiments, the disclosure provides in silico systems for drug development, such systems comprising, or alternatively consisting essentially of, or yet further consisting of at least one hardware processor and a non-transitory computer-readable storage medium having stored thereon program code, the program code executable by the at least one hardware processor to obtain data on genetic variants and phenotypes from each of a plurality of subjects, determine the value of the variant effects for each phenotype based on external data, construct a matrix based on the variants, phenotypes and values, run a principal components analysis on the variant x phenotype-related phenotype variant effects matrix, calculate a polygenic score for each principal component, and identify predicted drug effects on one or more phenotype based on the polygenic score calculated for each principal component.

In certain embodiments, the disclosure provides in silico systems for determination of intermediate phenotypes, such as risk factors or genetic variations that identify responders versus non-responders for a specific therapeutic intervention. Accordingly, in certain aspects, the disclosure provides in silico systems and methods for determining drug activity comprising, or alternatively consisting essentially of, or yet further consisting of obtaining data on genetic variants and phenotypes from each of a plurality of subjects, determining the value of the variant effects for each phenotype based on external data, calculating a polygenic score for a chosen phenotype intermediate in the disease process (e.g., a risk factor, biomarker, or genetic indicator of response), calculating a pharmacomimetic genetic score for each drug target; and identifying predicted drug activity on one or more phenotypes based on the statistical interaction of the polygenic score with the pharmacomimetic genetic score for each drug target in association analysis with the outcome phenotype.

In specific aspects, the disclosure provides methods in which the PRS information is provided in whole or in part from related disease phenotypes.

Accordingly, the disclosure provides a method of determining the drug activity of a drug target, comprising, or alternatively consisting essentially of, or yet further consisting of obtaining data on genetic variants and phenotypes from each of a plurality of subjects, determining the value of the variant effects for each phenotype based on external data, calculating a polygenic score for a chosen outcome phenotype related to the disease outcome, calculating a pharmacomimetic genetic score for the drug target, and identifying predicted drug activity of the drug target on one or more phenotypes based on the statistical interaction of the polygenic score with the pharmacomimetic genetic score for the drug target in association analysis with the outcome phenotype. The drug target may be, e.g., a known drug for the phenotype, a drug that has been approved or in trials for a different indication that the phenotype for which the analysis is being performed, or a de novo agent.

An aspect of the disclosure is directed to an in silico method for determining drug activity of a plurality of drug targets, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

In some embodiments, the plurality of drug targets is associated with a disease selected from Table 1. In some embodiments, the plurality of drug targets is associated with a disease selected from nonalcoholic steatohepatitis (NASH), coronary heart disease, dry age-related macular degeneration, rheumatoid arthritis, atopic disease, or obesity.

In some embodiments, the plurality of drug targets is associated with nonalcoholic steatohepatitis (NASH), and the plurality of drug targets comprises, or alternatively consists essentially of, or yet further consists of HSD17B13.

In some embodiments, the plurality of drug targets is associated with coronary heart disease, and the plurality of drug targets comprises, or alternatively consists essentially of, or yet further consists of LPL, ANGPTL4 and/or ANGPTL3.

In some embodiments, the plurality of drug targets is associated with dry age-related macular degeneration, and the plurality of drug targets comprises, or alternatively consists essentially of, or yet further consists of C3, CFB, CFH, and/or HTRA1.

In some embodiments, the plurality of drug targets is associated with rheumatoid arthritis, and the plurality of drug targets comprises, or alternatively consists essentially of, or yet further consists of TYK2.

In some embodiments, the plurality of drug targets is associated with atopic disease, and the plurality of drug targets comprises, or alternatively consists essentially of, or yet further consists of IL33, TSLP and/or IL4R.

In some embodiments, the plurality of drug targets is associated with obesity, and the plurality of drug targets comprises, or alternatively consists essentially of, or yet further consists of GLP1R and/or GIPR.

Another aspect of the disclosure is directed to an in silico method for determining drug activity of a plurality of drug targets, the method comprising:

obtaining molecular biomarker stratifier data and at least one disease phenotype from each of a plurality of subjects;

determining the value of the biomarker stratifier effects for each disease phenotype based on external data;

constructing a matrix based on the biomarker stratifiers, disease phenotypes and values;

running a principal components analysis biomarker stratifier x phenotype-related phenotype biomarker stratifier effects matrix;

calculating a biomarker stratifier score for each principal component;

calculating a pharmacomimetic genetic score for each drug target; and identifying predicted drug activity of each drug target on one or more phenotypes in subsets of the biomarker stratifier distribution based on the statistical interaction of the polygenic score calculated for each principal component with the pharmacomimetic genetic score for each drug target in association analysis with the outcome phenotype.

Another aspect of the disclosure is directed to an in silico method for determining the drug activity of drug targets on a plurality of phenotype intermediates, comprising: obtaining molecular biomarker stratifier data and disease phenotypes from each of a plurality of subjects;

determining the value of the biomarker stratifier effects for each phenotype intermediate based on external data;

calculating a biomarker stratifier score for each phenotype intermediate in the disease process;

calculating a pharmacomimetic genetic score for each drug target on each phenotype intermediate; and identifying predicted drug activity of the drug targets on one or more phenotypes in subsets of the biomarker stratifier distribution based on the statistical interaction of the biomarker stratifier score with the pharmacomimetic genetic score for each drug target in association analysis with the phenotype intermediate and the outcome phenotype.

Another aspect of the disclosure is directed to method of determining the drug activity of a drug target, comprising:

obtaining molecular biomarker stratifier data and disease phenotypes from each of a plurality of subjects;

determining the value of the biomarker stratifier effects for each phenotype based on external data;

calculating a biomarker stratifier score for a chosen outcome phenotype related to the disease outcome;

calculating a pharmacomimetic genetic score for the drug target; and identifying predicted drug activity of the drug target on one or more phenotypes in subsets of the biomarker stratifier distribution based on the statistical interaction of the biomarker stratifier score with the pharmacomimetic genetic score for the drug target in association analysis with the outcome phenotype.

Another aspect of the disclosure is directed to an in silico method comprising:

generating a plurality of principal components (PCs) corresponding to genetic ancestry data for subjects in a study cohort;

generating a biomarker stratifier score for each subject in the study cohort based at least on (i) the PCs and on (ii) biomarker stratifier weights for a disease of interest;

determining which of a plurality of disease-associated variants are pharmacomimetic instruments for the disease of interest, where a disease-associated variant is a pharmacomimetic instrument if the disease-associated variant modulates a function or expression of a target gene of a drug such that a first effect of the disease-associated variant on a phenotype is likely to be predictive of a second effect of the drug on the phenotype;

determining statistical interactions between the pharmacomimetic instruments for one or more drug targets and the biomarker stratifier scores, wherein the statistical interactions are predictive of drug target-specific differential treatment response for the disease of interest; and performing one or more prediction-based actions based on the determined interactions.

In some embodiments, the one or more prediction-based actions comprises at least one of (i) therapeutic development, (ii) therapeutic target identification, or (iii) pharmacogenomics.

In some embodiments, the genetic ancestry data indicates whether subjects in the study cohort are a case or a control for the disease of interest.

In some embodiments, the genetic ancestry data is based on genotyping arrays or whole-genome sequencing.

In some embodiments, the genetic ancestry data is obtained from a publicly-available database.

In some embodiments, the plurality of PCs comprises at least 5 PCs.

In some embodiments, the study cohort comprises at least 200 control subjects.

In some embodiments, each disease-associated variant in the plurality of disease-associated variants satisfies a genome-wide significance threshold.

In some embodiments, the plurality of disease-associated variants is determined based on a first disease genome-wide association study (GWAS).

In some embodiments, the biomarker stratifier score for each subject is a scaled biomarker stratifier score.

In some embodiments, the scaled biomarker stratifier score is based at least on a raw PGS and an ancestry-normalized PGS.

In some embodiments, the PGS variant weights are computed independent of the genetic ancestry data corresponding to the study cohort.

In some embodiments, determining which of the plurality of disease-associated variants are pharmacomimetic instruments for the disease of interest comprises generating an allelic score.

Another aspect of the disclosure is directed to an in silico system for drug development, such system comprising: at least one hardware processor; and a non-transitory computer-readable storage medium having stored thereon program code, the program code executable by the at least one hardware processor to:

obtain molecular biomarker stratifier data and disease phenotypes from each of a plurality of subjects;

determine the value of the biomarker stratifier effects for each phenotype based on external data;

construct a matrix based on the biomarker stratifiers, phenotypes and values;

run a principal components analysis biomarker stratifier x phenotype-related phenotype biomarker stratifier effects matrix;

calculate a biomarker stratifier score for each principal component;

calculate a pharmacomimetic genetic score for each drug target;

identify predicted drug effects on one or more phenotypes in subsets of the biomarker stratifier distribution based on the statistical interaction of the polygenic score calculated for each principal component with the pharmacomimetic genetic score for each drug target in association analysis with the outcome phenotype.

These and other embodiments, features, and advantages will be set forth in the present disclosure.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values or dimensions illustrated in the accompanying graphs and figures are for illustration purposes only and may or may not represent actual or preferred values or dimensions. Where applicable, some or all features may not be illustrated to assist in the description of underlying features.

FIG. 2 is a flow diagram showing the method of one embodiment of the disclosure.

FIG. 4 illustrates a flow diagram showing a method for in silico drug development and determination of drug activity in one embodiment of the disclosure.

FIG. 6 illustrates a flow diagram showing a method for in silico drug development and determination of drug activity in one embodiment of the disclosure.

DETAILED DESCRIPTION

Figure 1:
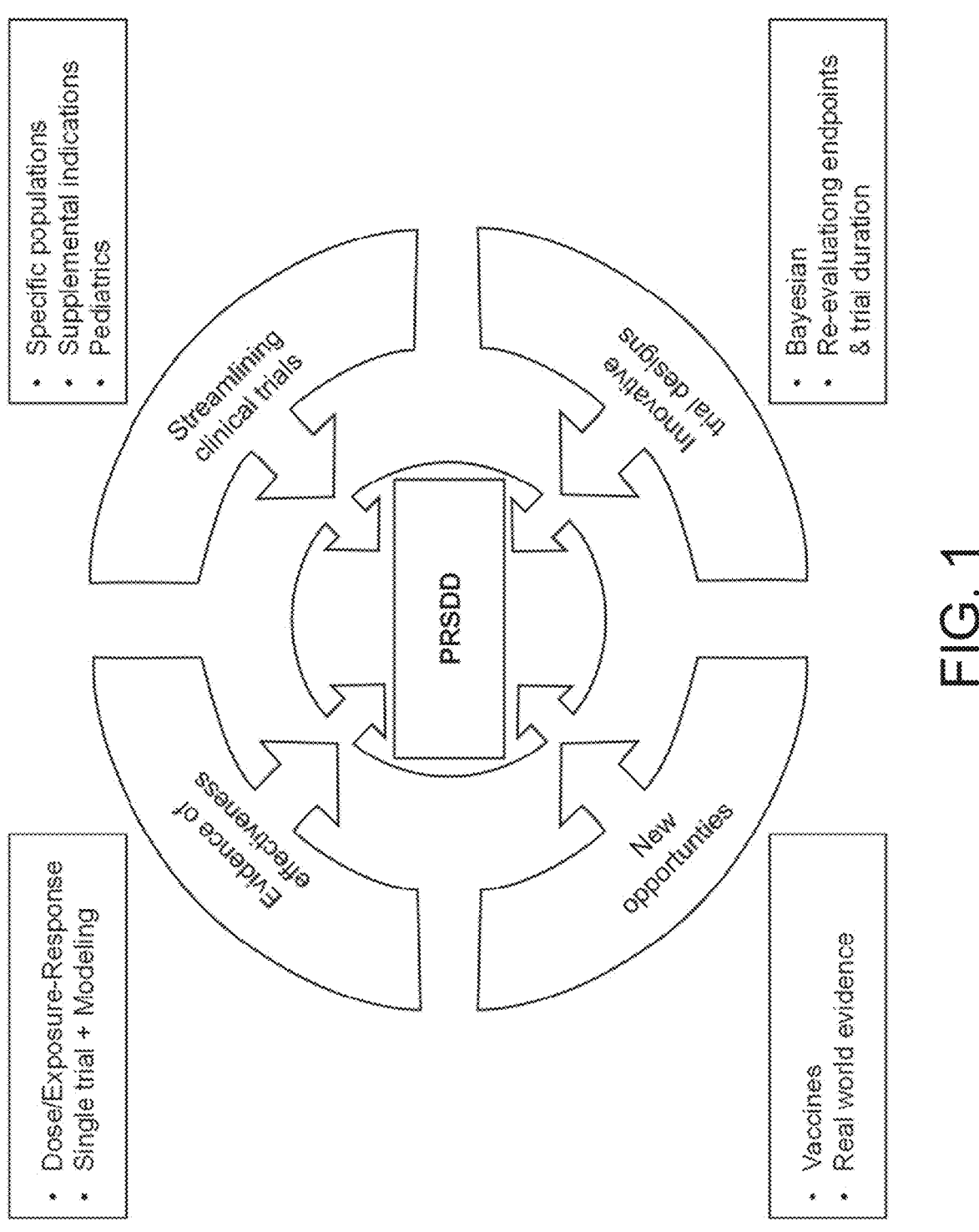
FIG. 1 is a schematic illustrating the potential applications of a polygenic risk score (or "polygenic score")-mediated drug development using the in silico systems of the present disclosure.

The following detailed description of preferred embodiments of the disclosure will be better understood when read in conjunction with the appended drawings.

The provided systems and methods are exemplified for coronary artery disease but are generalizable to use for PRS-informed drug development in any polygenic therapeutic area or indication; it will thus be understood by those of ordinary skill in the art that the present disclosure is exemplary and can be applied to other in silico systems and methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

In some aspects, the present disclosure describes in silico systems for recapitulation of empirical clinical trial data. Disclosure is provided herein demonstrating that genetic analysis using pharmacomimetic variants can recapitulate drug-PRS interactions observed in retrospective analyses of clinical trials. It also demonstrates that selectively enrolling patients with high PRS for clinical trials can increase average treatment response by enrolled patients as shown in the comparison of the empirical evidence and the results obtained by the systems of the disclosure. For example, as demonstrated, the average treatment response of a known anti-PCSK9 therapy can increase by a factor of ~2 in patients with high PRS.

Over the last decade, genome-wide association studies (GWAS) have uncovered the contribution of inherited variants to common complex disorders. Many non-communicable disorders with a major public health impact have a genetic underpinning that is highly polygenic, comprising, or alternatively consisting essentially of, or yet further consisting of hundreds or thousands of genetic variants (or polymorphisms), each having a small effect on disease risk. Each genetic variant associated with a disease is valuable in indicating a gene or pathway of biological relevance to the disorder, but there are also expectations that the genetic data could be used to predict disease risk, with potential clinical utility.

For example, there have been substantial successes in discovering and developing new health interventions, including therapeutics, for common chronic human diseases, here defined as diseases that have a prevalence in the general population of >0.1%. Despite these advances in management of common chronic diseases, there remains substantial unmet need in clinical areas that contribute significantly to the population burden of disease morbidity, premature mortality, and associated societal and healthcare costs. It is estimated that 6 in 10 Americans have at least one common chronic disease, and that these diseases collectively are responsible for ~$2.7T in US healthcare costs. Owing to substantial heterogeneity in disease progression and treatment response, drug development in these areas has required large clinical trials, at substantial clinical development cost, to evaluate clinical efficacy. Thus, despite substantial market opportunity and clinical unmet need, drug development has shifted over the last two decades to oncology and rare disease, where molecularly defined mechanisms and subpopulations have converged to enable a higher likelihood of demonstrating efficacy and safety sufficient for regulatory approval of new chemical entities.

Large scale genome-wide association studies performed over the last several decades have identified genetic contributions to variation in common disease risk, as well as the underlying risk factors that play a causal role in their pathobiology. These studies have found that the architecture of disease risk is genetically complex, reflecting the contributions of tens to millions of individual common genetic variants, each of small effect, as well as a smaller number of low frequency and rare genetic variants of greater effect. Collectively, these risk factors explain between ~40% and ~80% of the variation in disease risk observable at a population level. With larger studies of the effects of these genetic variants on disease risk has come an ability to more precisely estimate the contributions to disease risk of genetic variants at a range of effect sizes. This has facilitated the scaled summation of these effects into continuous polygenic genetic scores (PGS) that estimate, for any individual, the aggregate of measurable genetic risk. PGS may be isotropic, reflecting the sum total of genetic effects on disease risk agnostic to effects on underlying risk factors or biological pathways, or may reflect fundamental driver pathways in subsets of common chronic disease or in individuals with specific risk factors. Both isotropic as well as pathway- or risk-factor-specific PGS may resolve common disease heterogeneity and identify subgroups of the population who respond exceedingly well to certain therapeutic mechanisms. Indeed, there is clinical trial precedent for patients with high PGS receiving greater benefit from a drug than patients with low PGS. This phenomenon can be PGS-stratified drug efficacy. PGS-stratified drug efficacy was observed in clinical trials of PCSK9 antibodies for secondary prevention of cardiovascular disease (Marstonet al.2019, Damasket al.2019) and in a clinical trial of statins for primary prevention of cardiovascular disease (Natarajan 2017). In both cases, clinical benefit was magnified in individuals with high PGS.

A system implementing the systems and methods described herein may perform a method of analysis and use a knowledgebase for identifying individuals with subsets of common chronic human diseases who are predicted to enjoy greater benefit from specific therapeutic mechanisms. Specifically, the method identifies combinations of drug targets and disease indications where it is predicted that patients with a high PGS for the disease, its associated risk factors, or an aggregate of several genetically-driven biological pathways, will receive greater benefit from a drug compared to patients with a low PGS.

To perform the method, a computer may access genetic and phenotypic data for a large group of people (e.g., the "study cohort"). The genetic data can originate from genotyping arrays or whole-genome sequencing. The phenotype data does not have to come in a specific format. But, in some embodiments, phenotype data must be sufficient to determine whether each subject is a case, a control, or neither for the disease of interest. The algorithm for assigning case-control status to subjects may be manually defined by a user. The algorithm may consider, for example: (i) ICD-10 or ICD-9 diagnosis codes from hospital records or primary care records; (ii) self-reported diagnoses; (iii) medication prescriptions; and/or (iv) OPCS-4 or OPCS-3 operation codes from hospital records. The may computer may also use the age and sex of each subject. Examples of suitable study cohorts can include the UK Biobank, the FinnGen Research Project, and the All of Us Research Program. There is no exact requirement for the number of subjects in the study cohort, but typically the computer may use at least ~5 k cases and ~5 k controls for a particular disease of interest.

The computer may also access PGS variant weights for the disease of interest. "PGS variant weights" can refer to a table of genetic variants in which each genetic variant is assigned a weight (e.g., a numerical value). The weight can be an estimate of how much a given variant contributes to the risk of a disease. The computer can compute PGS variant weights using publicly available programs such as PRS-CS (Ge et al. 2019) or LDPred2 (Priveet al.2020). In some cases, PGS variant weights can be published by academic researchers. The computer can download such weights from a web resource called the PGS Catalog, for example. Computing the PGS variant weights may not involve any data from the study cohort and must be derived from a completely independent dataset, in some embodiments.

The computer may access results from a genome-wide association study (GWAS) for the disease of interest, commonly referred to as "summary statistics." To do so, the computer may retrieve GWAS summary statistics from a web resource, such as the EBI GWASCatalog, for example. Alternatively, the data processing system may perform the GWAS within the study cohort, such as by using publicly available software such as Plink (Purcellet al.2007, Changet al.2015), SAIGE (Zhouet al.2018), or REGENIE (Mbatchouet al.2021).

The computer can access a computational pipeline for mapping GWAS variants to causal genes, such as the pipelines published by Mountjoyet al.2021 and Gazalet al.2022. The drug-by-PGS interaction discovery method is agnostic to the particular pipeline that is used.

The method can apply the following operations of a framework: (1) modeling the predicted effects of drug target modulation from genotype-phenotype association analysis of human genetic variants in drug target-encoding genes and observed clinical phenotypes. The genetic variants used for modeling may be individual variants or sets of statistically-independent variants in the same drug target gene identified as "allelic scores." These statistical instruments are "pharmacomimetic instruments;" (2) partitioning a human population according to isotropic PGS, risk factor PGS, or biological pathway-PGS; and (3) application of a method for identifying statistical interactions between pharmacomimetic instruments for drug targets and PGS that predict drug target-specific differential treatment response. In some embodiments, the method can include using the predicted drug target-specific differential treatment response to select patients for treatment and/or applying the treatment. In some embodiments, the method can include transmitting the predicted drug target-specific differential treatment response and/or any data used to determine the predicted drug target-specific differential treatment response (e.g., the statistical interactions, the determined PGS, etc.) to another computing system (e.g., into a downstream pipeline) for an entity associated with the computing system to use for treatment.

In performing the aforementioned method, a computing system can use human genetic data to predict a-priori whether a given drug mechanism will exhibit PGS-stratified efficacy without needing to have clinical trial data. For example, the computing system can use the predictive ability of the method by applying the method to modeling the effects of the anti-PCSK9 mechanism on the risk of cardiovascular disease according to PGS, accurately recapitulating the results of clinical trial data. The computing system can use the method on at least 35 common chronic diseases to identify and/or implement novel indications for drug targets in which PGS stratification is likely to yield differential treatment response. The computing system can use the method to identify or use PGS-stratified efficacy LDL-lowering therapies (e.g., statins and PCSK9 antibodies) in cardiovascular disease as well as drugs for a wide variety of indications.

FIG. 1 illustrates a schematic illustrating the potential applications of a polygenic risk score (or "polygenic score")-mediated drug development in one embodiment of the disclosure.

FIG. 2 is a flow diagram showing a method 200 of one embodiment of the disclosure. The method 200 can be performed by a data processing system (e.g., a client device or the data processing system 302, shown and described with reference to FIG. 3, a server system, etc.). The method 200 may include more or fewer operations and the operations may be performed in any order. Performance of the method 200 may enable the data processing system to automatically identify predicted drug effect on phenotypes based on polygenic risk scores.

In the method 200, at operation 202, the data processing system obtains genetic variant data from a plurality of subjects with identified phenotypes. At operation 204, the data processing system determines the value of the variant effects for each phenotype based on external data. At operation 206, the data processing system constructs a matrix based on the variants, phenotypes, and values of the variant effects. At operation 208, the data processing system runs a principal components analysis biomarker variant x phenotype-related phenotype variant effects matrix. At operation 210, the data processing system calculates a polygenic risk score for each principal component. At operation 212 the data processing system identifies predicted drug effects on one or more phenotypes based on the polygenic risk scores calculated for each principal component.

Figure 3:
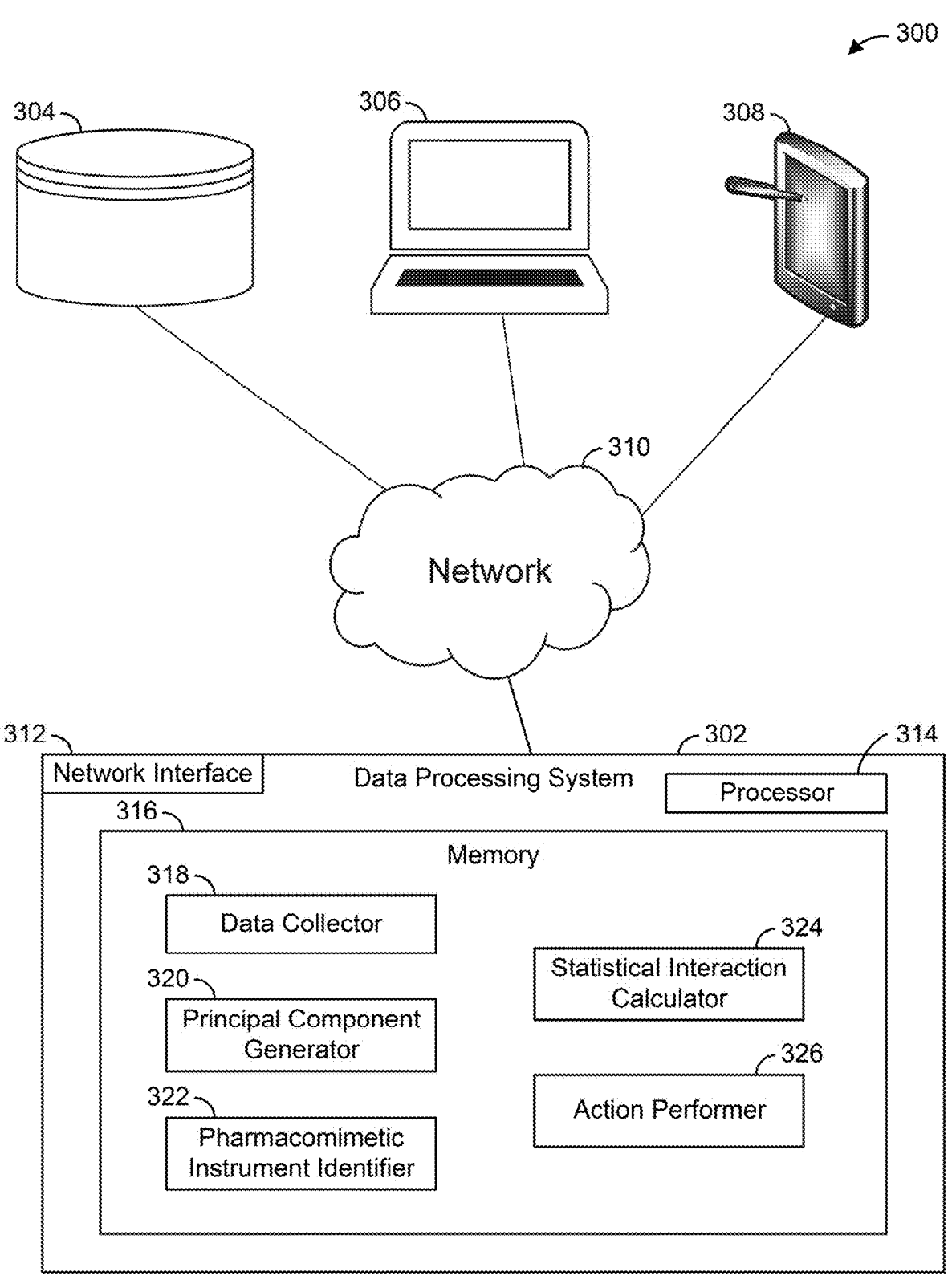
FIG. 3 illustrates a block diagram of a system for in silico drug development and determination of drug activity in one embodiment of the disclosure.

FIG. 3 illustrates a block diagram of a system 300 for in silico drug development and determination of drug activity in one embodiment of the disclosure. In brief overview, the system 300 can include a data processing system 302 and data sources 304, 306, and 308. The data processing system 302 can receive or retrieve molecular biomarker stratifier data of a plurality of subjects. The data processing system 302 can determine values representing biomarker stratifier effects based on external data of individuals separate from the plurality of subjects. The data processing system 302 can calculate a biomarker stratifier score, a chosen disease phenotype and a pharmacomimetic genetic score for different drug targets. The data processing system 302 can identify a predicted drug activity for each drug target based on the biomarker stratifier score and the pharmacomimetic genetic score for the drug target in association analysis with the disease phenotype. The system 300 may include more, fewer, or different components than shown in FIG. 3.

The data processing system 302 may comprise one or more processors that are configured to identify predicted drug activity for drug targets for disease phenotypes. The data processing system 302 may comprise a network interface 312, a processor 314, and/or memory 316. The data processing system 302 may communicate with the data sources 304, 306, and/or 308 via the network interface 312, which may be or include an antenna or other network device that enables communication across a network and/or with other devices. The processor 314 may be or include an ASIC, one or more FPGAs, a DSP, circuits containing one or more processing components, circuitry for supporting a microprocessor, a group of processing components, or other suitable electronic processing components. In some embodiments, the processor 314 may execute computer code or modules (e.g., executable code, object code, source code, script code, machine code, etc.) stored in memory 316 to facilitate the activities described herein. The memory 316 may be any volatile or non-volatile computer-readable storage medium capable of storing data or computer code.

The memory 316 may include a data collector 318, a principal component (PC) generator 320, a pharmacomimetic instrument identifier, a statistical interaction calculator 324, and/or an action performer 326, in some embodiments. The components 318-326 may operate to identify predicted drug activity of drug targets for different disease phenotypes.

For example, the data collector 318 may comprise programmable instructions that, upon execution, cause the processor 314 to communicate with the data sources 304, 306, 308, and/or any other data sources. The data collector 318 may be or include an application programming interface (API) that facilitates communication between the data processing system 302 and other computing devices. The communicator 318 may communicate with the data sources 304, 306, 308, and/or any other computing device across the network 310.

The data sources 304, 306, and 308 can be data sources that store molecular biomarker stratifier data and/or external data. For example, the data sources 304, 306, and/or 308 can be or include a database (e.g., a relational or graph database) that stores molecular biomarker stratifier data that includes biomarker stratifiers and at least one disease phenotype from or of a plurality of subjects or individuals. The data sources 304, 306 and/or 308 can additionally or instead include external data of individuals separate from the plurality of subjects or individuals of molecular biomarker stratifier data.

The data collector 318 can establish connections with one or more of the data sources 304, 306, and/or 308. The data collector 318 can establish the connections over the network 310. To do so, the data collector 318 can communicate with the data sources 304, 306, and/or 308 across the network 310. In one example, the data collector 318 can transmit syn packets to the respective data sources 304, 306, and/or 308 and establish the connections using a TLS handshaking protocol. The data collector 318 can use any handshaking protocol to establish a connection with the data sources 304, 306, and/or 308.

The data collector 318 can obtain the molecular biomarker stratifier data and the external data. In some embodiments, the data collector 318 can obtain the molecular biomarker stratifier data and the external data over the established connections from one or more of the data sources 304, 306, or 308. The data collector 318 may do so by querying the data sources 304, 306, or 308. In some embodiments, the data collector 318 can receive the molecular biomarker stratifier data and/or the external data as input (e.g., a manual input) by a user accessing the data processing system. The data collector 318 can obtain portions of the molecular biomarker stratifier data and the external data using any method or any combination of methods.

The PC generator 320 may comprise programmable instructions that, upon execution, cause the processor 314 to generate principal components. The PC generator 320 can generate principal components that correspond to (or based on) genetic ancestry data (e.g., different genes) for subjects in a study cohort. The genetic ancestry data can be based on genotyping arrays or whole-genome sequencing. The PC generator 320 can obtain the genetic ancestry data from a publicly available database, as described herein. The PC generator 320 can be FlashPCA, for example. The principal components can be used to control subsequent statistical analyses for population stratification, in some embodiments.

For example, the PC generator 320 can generate a plurality of PCs corresponding to genetic ancestry data for subjects in a study cohort. The PC generator 320 can do so by generating a genetic similarity matrix from the genetic ancestry data of the subjects in the study cohort and using principal component analysis on the genetic similarity matrix. The PC generator 320 can generate any number of PCs using principal components analysis.

The PC generator 320 can generate a biomarker stratifier score for each subject in the study cohort. The PC generator 320 can generate the biomarker stratifier scores based at least on (i) the PCs and on (ii) biomarker stratifier weights for a disease of interest. For example, a "raw PGS" (e.g., a biomarker stratifier score) for a subject S can be defined as the sum over each variant in a PGS variant weights table of ((the variant's weight)*(the # of copies S has of that variant)). The PGS variant weights of the PGS variant weights table can be computed independent of the genetic ancestry data corresponding to the study cohort. The PC generator 320 can generate biomarker stratifier scores for any number of diseases, such as nonalcoholic steatohepatitis (NASH), coronary heart disease, dry age-related macular degeneration, rheumatoid arthritis, atopic disease, and/or obesity.

The PC generator 320 can determine "ancestry-normalized" PGS. The PC generator 320 can determine the ancestry-normalized PGS to be the residuals of a linear regression model where the outcome can be the raw PGS and the predictors are the PCs of genetic ancestry data. This normalization can correct for differences in mean PGS values between populations. The ancestry-normalized PGS can also be called an ancestry-normalized biomarker stratifier score.

The PC generator 320 can determine "Scaled PGS." The PC generator 320 can do so using the following equation: scaled PGS=((the ancestry-normalized PGS–the ancestry-normalized PGS across all subjects in the cohort)/(the standard deviation of the ancestry-normalized PGS across all subjects in the cohort)). Scaled PGS values can thus be approximately normally distributed. The scaled PGS can be used for all subsequent analyses. Scaled PGSs are also called scaled biomarker stratifier scores.

The pharmacomimetic instrument identifier 322 may comprise programmable instructions that, upon execution, cause the processor 314 to determine which of a plurality of disease-associated variants are pharmacomimetic instruments for the disease of interest. A disease-associated variant can be a pharmacomimetic instrument if the disease-associated variant modulates a function or expression of a target gene of a drug such that a first effect of the disease-associated variant on a phenotype is likely to be predictive of a second effect of the drug on the phenotype.

To determine which of the plurality of disease-associated variants are pharmacomimetic instruments for the disease of interest, the pharmacomimetic instrument identifier 322 may execute a program (e.g., GCTA COJO-SLCT) for the disease of interest to identify "conditionally independent disease-associated variants." To do so, for example, the pharmacomimetic instrument identifier 322 may first run a GWAS (e.g., a first GWAS) as normal. The pharmacomimetic instrument identifier 322 can identify the variant that has the most significant association with the disease outcome (e.g., the smallest p-value) across the whole genome. The pharmacomimetic instrument identifier 322 can rerun the GWAS, this time conditioning all of the variant-disease association tests on the genotype of the most-significant variant. The pharmacomimetic instrument identifier 322 can identify the variant that has the next-most significant association with the disease outcome. The pharmacomimetic instrument identifier 322 can rerun the GWAS, this time conditioning all of the variant-disease association tests on the genotype of the most-significant and the 2nd-most-significant variants. The pharmacomimetic instrument identifier 322 can iteratively repeat this procedure until determining no variant is associated with the disease below a defined p-value threshold (e.g., a genome-wide significance threshold, such as $5 \times 10^{-8}$). Using lower thresholds can reduce the chances that an analytical result is a fluke, but increases the chance that the data processing will not identify an important variant, and vice versa. The pharmacomimetic instrument identifier 322 can use any threshold. The set of variants identified by the pharmacomimetic instrument identifier can be called "conditionally-independent disease-associated variants" because each variant is associated with the disease even after conditioning on the genotypes of all of the previous variants.

The pharmacomimetic instrument identifier 322 can create a table. Each row of this table can correspond to one subject from the study cohort and include data regarding the subject such as demographic data and other determined data (e.g., PGS, PCS of genetic ancestry, dosage for the alternate allege of each of the independent disease associated variants, etc.).

The pharmacomimetic instrument identifier 322 can identify which of the conditionally-independent disease-associated variants are "pharmacomimetic instruments" (e.g., variants that modulate the function or expression of a drug target gene so that the variants' effect on human phenotypes is likely to be predictive of the drug's effect on human phenotypes). Depending on the configuration, the pharmacomimetic instrument identifier 322 can use different criteria and/or priorities to identify pharmacomimetic instruments from the identified conditionally-independent disease-associated variants. In one example, a user may be interested in clinical-stage drugs for the disease. In this case, the pharmacomimetic instrument identifier 322 can compile a table of clinical-stage drugs and their targets using public resources, such as clinicaltrials.gov and/or proprietary databases, such as Cortellis. The pharmacomimetic instrument identifier 322 can determine that variants that are close to a drug target gene (e.g., within 150 kb of the gene's transcription start site) or are mapped to the drug target are pharmacomimetic instruments. In another example, a user may be interested in known and novel drug targets for the antibody modality. In this case, the pharmacomimetic instrument identifier 322 can compile a list of genes that encode proteins that are druggable with the antibody modality (e.g., proteins that are secreted or localized to the cell surface). The pharmacomimetic instrument identifier 322 can determine variants that are mapped to an antibody-druggable protein are pharmacomimetic instruments based on the compiled table (e.g., based on the determined variants having stored associations with the antibody-druggable protein).

In some embodiments, there is more than one suitable variant for a drug mechanism. In this case, it will increase statistical power to detect drug-PGS interactions by aggregating variants (e.g., all of the variants) identified as pharmacomimetic instruments that were associated with a given drug mechanism into a combined allelic score. To do so, for example, the pharmacomimetic instrument identifier 322 can compute an allelic score in the same or a similar manner to a PGS (e.g., assign each variant a weight and compute, for each subject in the cohort, the sum over each variant of (the variant's weight)*(the subject's dosage for the variant)). The difference between an allelic score and a PGS is that the allelic score is composed of variants that modulate the function or expression of a single drug target gene, while a PGS can be composed of variants across the genome that affect many different genes. The variants in the allelic score may be weighted using a GWAS (e.g., a second GWAS) for the disease that did not include any subjects from the study cohort. Alternatively, the variants can be weighted using a GWAS (e.g., a third GWAS) for a biomarker that causally mediates the effect of the drug target on the disease (e.g., LDL cholesterol mediates the effect of PCSK9 on coronary artery disease). A biomarker GWAS still must not overlap the study cohort.

The statistical interaction calculator 324 may comprise programmable instructions that, upon execution, cause the processor 314 to determine statistical interactions between the pharmacomimetic instruments for one or more drug targets and the biomarker stratifier scores. The statistical interactions can be predictive of drug target-specific differential treatment responses for the disease of interest. To determine the statistical interactions, the statistical interaction calculator 324 can generate a data table with phenotypes, covariates, and a set of pharmacomimetic instruments determined using the aforementioned systems and methods, which may include single variants and multi-variant allelic scores. Responsive to doing so, the statistical interaction calculator 324 can test for interactions between the pharmacomimetic instruments and the PGS in association analysis with the disease or risk factor trait of interest.

For example, for each pharmacomimetic instrument, the statistical interaction calculator 324 can use statistical software, such as the R programming language, to fit a logistic regression model using the following example formula: disease case-control status~age+sex+ancestry PCs+(pharmacomimetic instrument)+(scaled PGS)+(pharmacomimetic instrument):(scaled PGS). In doing so, the statistical interaction calculator 324 can determine the scaled PGS. The model can be implemented using the R programming language, such as by using the command glm(model_formula, family="binomial", data=our_genetic_and_phenotypic_data). In the example formula, the variable to the left of the "~" symbol is the dependent variable (e.g., the variable that is being predicted). Each of the variables to the right of the "~" symbol, separated by "+" symbols, are independent variables, (e.g., variables that are observed in the data and used to predict the dependent variable). The ":" symbol indicates a variable that is the product (result of multiplication) of the variables to the left and right of the ":" symbol. This product is an "interaction term." If the pharmacomimetic instrument:scaled polygenic score (PGS) interaction term—one of the independent variables—has a statistically-significant association with the dependent variable (in this case, disease status), controlling for all of the other independent variables—such as age and sex—then the statistical interaction calculator 324 can predict or determine that the drug that is modeled by the pharmacomimetic instrument will have different effects in subjects with high PGS vs. low PGS. The statistical interaction calculator 324 can fit a logistic regression model for each pharmacomimetic instrument that the pharmacomimetic instrument identifier 322 determines or identifies.

The statistical interaction calculator 324 can use the same program to compute a p-value for the interaction term. If the p-value for the interaction between a pharmacomimetic instrument and the PGS is <0.05/(the # of instruments tested), the statistical interaction calculator 324 can determine the interaction to be "Bonferroni significant". Alternatively, the statistical interaction calculator 324 can be configured to use a more lenient p-value threshold, at the risk of false positives.

The instrument-PGS interactions can be "drug-PGS interactions" because each pharmacomimetic instrument is a model for a particular drug mechanism.

The statistical interaction calculator 324 can generate tables that present the statistically significant drug-PGS interactions in a way that is easier to interpret than looking at the raw regression model outputs. For example, first, the statistical interaction calculator 324 can group the subjects of the study cohort by quantiles of the PGS, (e.g., the 0-33rd percentile, the 34th-66th percentile, and the 67th-100th percentile). Then, for each drug-PGS interaction, the statistical interaction calculator 324 can fit separate logistic regression models within each PGS quantile using the formula: disease case-control status~age+sex+ancestry PCs+the pharmacomimetic instrument for the drug. Using these regression outputs, the statistical interaction calculator 324 can construct a table that shows the effect of the pharmacomimetic instrument on disease risk (as well as a 95% confidence interval for that effect) within each PGS quantile.

For instance, the statistical interaction calculator 324 can divide the subjects of the study into a finite number of groups (e.g., the groups) based on their PGS values. Within each group, the statistical interaction calculator 324 can predict a disease outcome based on the patients' genetics, specifically a genetic instrument that mimics the effects of a drug (the "pharmacomimetic instrument"). In doing so, the statistical interaction calculator 324 can determine a difference in how strongly the pharmacomimetic instrument predicts the disease outcome in individuals with high PGS vs. middle PGS vs. low PGS. The difference may indicate that a drug might have different efficacy in people with high PGS vs. middle PGS vs. low PGS.

The statistical interaction calculator 324 can also compute a statistic called the "treatment effect multiplier." This is the effect of the pharmacomimetic instrument on disease risk in the top quartile divided by the effect in all subjects. The "treatment effect multiplier" can represent how much one could increase the average treatment effect in a clinical trial of the drug if one enrolled only patients in the top quantile of the PGS as opposed to enrolling all qualified patients. The treatment effect multiplier is a way to compare drug-PGS interactions to distinguish "strong" from "weak" interactions.

The action performer 326 may comprise programmable instructions that, upon execution, cause the processor 314 to perform one or more prediction-based actions based on the determined interactions. The one or more prediction-based actions can include at least one of (i) therapeutic development, (ii) therapeutic target identification, or (iii) pharmacogenomics. To perform a prediction-based action, the action performer 326 can select a patient for treatment. The action performer 326 can select the patient based on a likelihood that the patient will benefit from the treatment. For example, the action performer 326 can select the patient by determining a PGS for the patient using the systems and methods described herein and determining the PGS for the patient is above a threshold (e.g., a PGS threshold) or within a range (e.g., a quartile, a quintile, a defined range, etc.). In another example, the action performer 326 can select patients for novel therapeutic mechanisms whose benefit is mostly or only apparent in subsets of common disease patients who have elevated polygenic risk. This enables novel target identification and novel therapeutic discovery.

In another example, the action performer 326 can select patients from large common disease treatment-eligible populations who will benefit most from existing drug therapies, and, conversely, identify patients who are not likely to receive clinically meaningful benefit. This can enhance the pharmaco-economic profile of existing therapeutic mechanisms, yielding more cost-effective utilization. In another example, the action performer 326 can select mechanisms and design of prospective clinical trials of investigational drugs that are predicted to yield greater benefit in individuals with elevated PGS. These trials may be run with many-fold fewer patient years required to demonstrate clinical benefit, given the expectation of magnified event rate and treatment response rates.

In some embodiments, treatment can be performed on the selected patients. For example, the action performer 326 can select patients with PGS scores that satisfy a criteria for a particular treatment to treat a disease. Examples of such treatment can be treatment for NASH, coronary heart disease, dry age-related macular degeneration, rheumatoid arthritis, atopic disease, and/or obesity. The action performed 326 can generate a record that includes a list of selected patients. An entity (e.g., a user or a clinician) may view the list and apply a treatment for the disease to the patients identified in the record. Examples of such treatment can include injections, therapy, or other treatment techniques. In some embodiments, the action performer 326 can connect with another computer and transmit the record containing the list of patients or the PGS scores determined by the PC Generator 320 to another computer. The computer may display the scores or list of patients and the entity or user accessing the computer may use the list and/or scores to for treatment.

FIG. 4 illustrates a flow diagram showing a method 400 for in silico drug development and determination of drug activity in one embodiment of the disclosure. The method 400 can be performed by a data processing system (e.g., a client device or the data processing system 302, shown and described with reference to FIG. 3, a server system, etc.). The method 400 may include more or fewer operations and the operations may be performed in any order. Performance of the method 400 may enable the data processing system to automatically identify predicted drug activity of different drug targets for disease phenotypes and/or phenotype intermediates.

In the method 400, at operation 402, the data processing system obtains molecular biomarker stratifier data. The molecular biomarker stratifier data can include a plurality of biomarker stratifiers and at least one disease phenotype or phenotype intermediate from each of a plurality of subjects. The molecular stratified biomarker data can include at least one of the following types of data: genomic, transcriptomic, metabolomic, or proteomic. These data are obtained by assays specific to each biomarker type. The at least one disease phenotype or phenotype intermediate can include or be associated with nonalcoholic steatohepatitis (NASH), coronary heart disease, dry age-related macular degeneration, rheumatoid arthritis, atopic disease, and/or obesity.

The molecular biomarker stratifier data can include data on the at least one disease phenotype. The data can include a patient's disease status (e.g., has been diagnosed with CAD yes/no) at a given point in time. The data can also include quantitative disease traits (e.g., LDL, HDL, and Tg measurements at a given time with regard to disease diagnosis), medication information (e.g., patient has taken or is taking a statin or other lipid-lowering therapy at a given time with regard to disease outcomes), and demographic information (e.g., age at diagnosis, biological sex, etc.).

At operation 404, the data processing system determines a plurality of values (e.g., numeric values) representing biomarker stratifier effects. Each value can separately represent how each of the plurality of biomarker stratifiers affects each of the at least one disease phenotype or phenotype intermediate. The biomarker stratifier effects can respectively be the estimated magnitude of effect of the biomarker on disease risk or continuous disease trait from a statistical model. The data processing system can determine the plurality of values based on external data (e.g., data regarding individuals separate from the subjects of the plurality of subjects). The data processing system can determine the plurality of values using a logistic regression model for disease (yes/no) vs. biomarker (e.g., protein measurement)+covariates (age, sex, etc.) on the data.

At operation 406, the data processing system calculates a biomarker stratifier score for a chosen disease phenotype or phenotype intermediate. The data processing system can calculate a biomarker stratifier score for each of the at least one disease phenotype or phenotype intermediate. The data processing system can determine biomarker stratifier scores as polygenic risk scores for individual disease phenotypes. The data processing system can calculate biomarker stratifier scores for biomarker stratifiers. In doing so, for example, the data processing system can determine a biomarker stratifier score as one of the following: a polygenic risk score for the disease phenotypes; a polygenic score for a disease risk factor; a polygenic score for biological pathway activity; a polygenic score for drug target expression; a proteomics risk score for the disease phenotypes; a proteomics score for a disease risk factor; a proteomics score for biological pathway activity; a proteomics score for drug target expression; a transcriptomics risk score for the disease phenotypes; a transcriptomics score for a disease risk factor; a transcriptomics score for a biological pathway activity; a somatic mutation score for drug target expression; a somatic mutation score for the disease phenotypes; a somatic mutation score for a disease risk factor; a somatic mutation score for a biological pathway activity; or a somatic mutation score for drug target expression. For instance, if the stratifier is a polygenic risk score (PRS), a statistical model may be trained using summary statistics from a published study on large-scale cohorts or from a meta-analysis of multiple studies based on large and diverse set of cohorts (none of which include UK Biobank). The data processing system can apply the estimated weights from that model to a dataset that is orthogonal to the ones used for training (e.g., UK Biobank).

At operation 408, the data processing system calculates a pharmacomimetic genetic score for each drug target for which the data processing system is determining a drug activity. The pharmacomimetic genetic score can represent genes for which more than one pharmacomimetic variant (e.g., a functional variant in a gene that is strongly and significantly associated with a given disease) are identified. The data processing system can determine the pharmacomimetic genetic score by weighting each variant by its estimated effect on the phenotype and summing the weighted values.

At operation 410, the data processing system identifies the predicted drug activity of each drug target for the at least one disease phenotype or phenotype intermediate in subsets of a biomarker stratifier distribution. The data processing system can identify the predicted drug activity based on a statistical interaction of the biomarker stratifier score with the pharmacomimetic genetic score for each drug target in association analysis with the disease phenotype or phenotype intermediate. For example, the data processing system can use a model (e.g., a linear regression model, a logistic regression model, a Cox Proportional Hazards model, etc.) that includes a predictor defined by the multiplicative interaction between the pharmacomimetic genetic score and biomarker score to perform the association analysis for each drug target and disease outcome phenotype. The predictor can be the predicted drug activity.

The data processing system can identify the subsets of the biomarker stratifier distribution using one or more thresholds. The one or more thresholds can be chosen to define different subsets depending on the use case. In one example, it may be optimal to use a 25th percentile of the CAD polygenic risk score to define a subset of patients who are predicted to have an outsized clinical benefit from therapy X. In another example, it may be optimal to use a 33% (top tertile) of the CAD PRS to define a subset of patients who would benefit most from therapy Y. In other disease settings with different PRS, the thresholds may also vary. Defining the optimal threshold will depend on factors such as: estimated effect size for the subset vs. all-corners on therapy, failure screening rate (in a trial, if the threshold is set too conservatively, e.g., 5%, a lot more patients will have to be screened to enroll a few), etc. Subsets can be from individual-level cohort data as the top 10%, 20%, 30%, etc. of the distribution.

Figure 5:
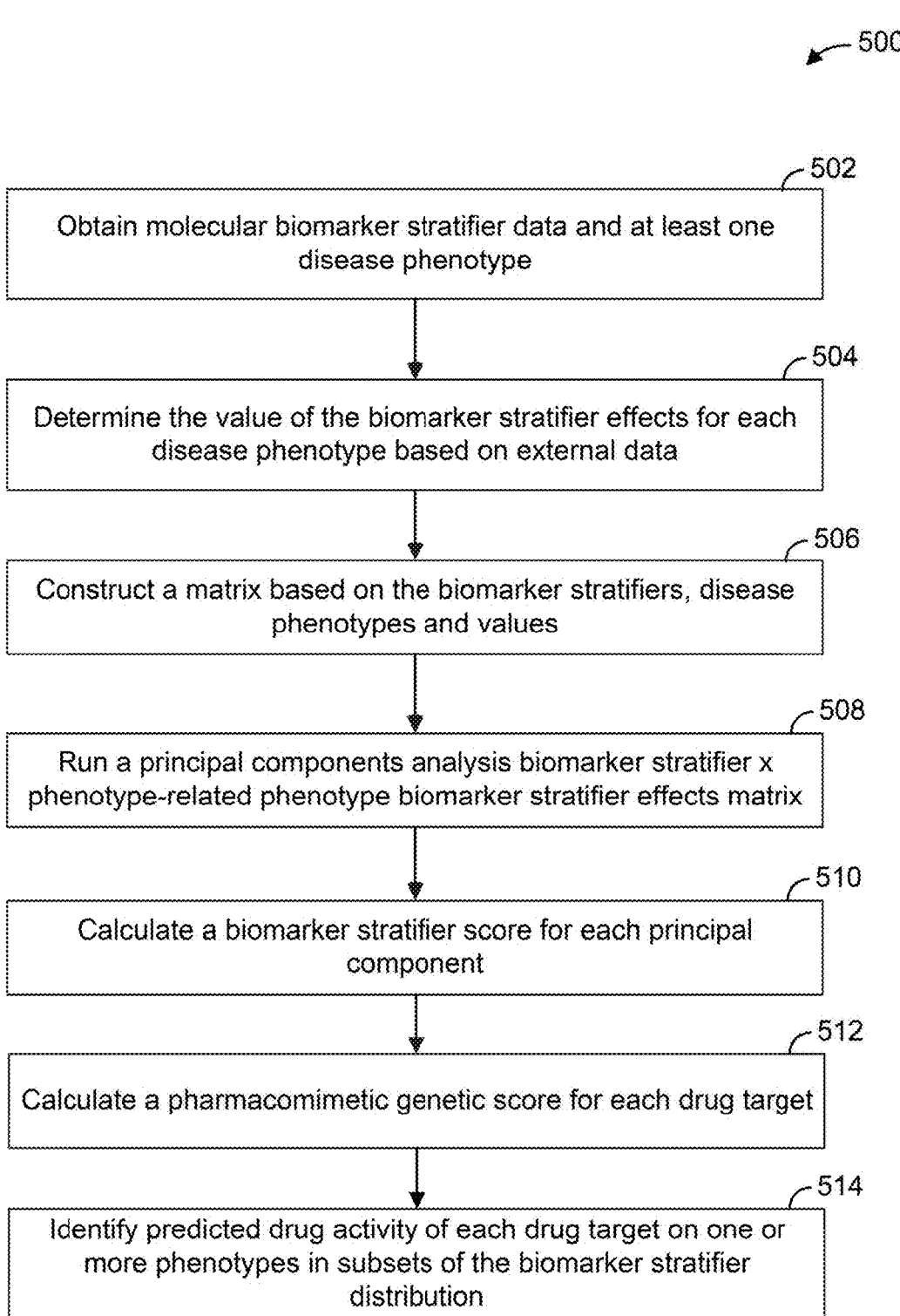
FIG. 5 illustrates a flow diagram showing a method for in silico drug development and determination of drug activity in one embodiment of the disclosure.

FIG. 5 illustrates a flow diagram showing a method 500 for in silico drug development and determination of drug activity in one embodiment of the disclosure. The method 500 can be performed by a data processing system (e.g., a client device or the data processing system 302, shown and described with reference to FIG. 3, a server system, etc.). The method 500 may include more or fewer operations and the operations may be performed in any order. Performance of the method 500 may enable the data processing system to automatically identify predicted drug activity of different drug targets for disease phenotypes or phenotype intermediates.

In the method 500, at operation 502, the data processing system obtains molecular biomarker stratifier data and at least one disease phenotype or phenotype intermediate. The molecular biomarker stratifier data can include a plurality of biomarker stratifiers. The data processing system can obtain the molecular biomarker stratifier data from each of a plurality of subjects.

At operation 504, the data processing system determines the value of the biomarker stratifier effects for each disease phenotype or phenotype intermediate. Each value can separately represent how each of the plurality of biomarker stratifiers affects each of the at least one disease phenotype or phenotype intermediate. The data processing system can determine the plurality of values based on external data (e.g., data regarding individuals separate from the subjects of the plurality of subjects). At operation 506, the data processing system constructs a matrix based on the biomarker stratifier data (e.g., biomarker stratifiers), disease phenotypes or phenotype intermediate values. At operation 508, the data processing system runs a principal components analysis biomarker stratifier phenotype-related x phenotype biomarker stratifier effects matrix. At operation 510, the data processing system calculates a biomarker stratifier score for each principal component. At operation 512, the data processing system calculates a pharmacomimetic genetic score for each drug target. At operation 514, the data processing system identifies predicted drug activity of each drug target on one or more phenotypes or phenotype intermediates in subsets of the biomarker stratifier distribution. The data processing system can identify the predicted drug activity based on a statistical interaction of the polygenic score calculated for each principal component with the pharmacomimetic genetic score for each drug target in association analysis with the outcome phenotype or outcome phenotype intermediate.

FIG. 6 illustrates a flow diagram showing a method 600 for in silico drug development and determination of drug activity in one embodiment of the disclosure. The method 600 can be performed by a data processing system (e.g., a client device or the data processing system 302, shown and described with reference to FIG. 3, a server system, etc.). The method 600 may include more or fewer operations and the operations may be performed in any order. Performance of the method 600 may enable the data processing system to automatically determine interactions between pharmacomimetic instruments and perform prediction-based actions based on the determined interactions. One or more of the operations in the methods 400, 500, and/or 600 can be performed during operations in any other of the methods 400, 500, and/or 600.

In the method 600, at operation 602, the data processing system generates a plurality of principal components (PCs) corresponding to genetic ancestry data (e.g., genetic data) for subjects in a study cohort. The data processing system can generate any number of PCs. For example, the data processing system can generate five PCs, at least six PCs for a European ancestry cohort, and/or 10-to-40 PCs for a multi-ancestry cohort (e.g., 20 for UK Biobank and/or possibly up to 40 for a more diverse cohort). The study cohort can include at least 200 control subjects. In some embodiments, the study cohort can include at least 950 control subjects or at least 990 control subjects. The data processing system can determine whether subjects in the study cohort are a case or a control for a disease of interest, such as based on flags for the subjects that indicate whether the subjects are cases or controls. The genetic ancestry data can be based on genotyping arrays or whole-genome sequencing. The data processing system can obtain the genetic ancestry data from a publicly available database, for example, or through any other method.

At operation 604, the data processing system generates a biomarker stratifier score for each subject in the study cohort. The data processing system can generate the biomarker stratifier scores based at least on (i) the PCs and on (ii) biomarker stratifier weights for a disease of interest. The biomarker stratifier score can be for the particular disease of interest. For example, a "raw PGS" (e.g., a biomarker stratifier score) for a subject S can be defined as the sum over each variant in a PGS variant weights table of ((the variant's weight)*(the # of copies S has of that variant)). For example, consider three variants A, B, and C, with weights 1, 2, and 3 respectively. If subject S has 2, 0, and 1 copies of variants A, B, C, then their unscaled PGS is computed as 2*weight(A)+0*weight(B)+1*weight(C)=2*1+0*2+1*3=5. The PGS variant weights can be computed independent of the genetic ancestry data corresponding to the study cohort.

The data processing system can determine "ancestry-normalized PGSs." Ancestry-normalized PGS can be defined as the residuals of a linear regression model where the outcome can be the raw PGS and the predictors are the PCs of genetic ancestry that were selected in operation 602. This normalization can correct for differences in mean PGS values between populations.

The data processing system can determine "scaled PGSs." Scaled PGS can be defined as ((the ancestry-normalized PGS—the ancestry-normalized PGS across all subjects in the cohort)/(the standard deviation of the ancestry-normalized PGS across all subjects in the cohort)). Scaled PGS values can thus be approximately normally distributed. The scaled PGS can be used for all subsequent analyses. The task of creating and scaling PGS that is effective and comparable across populations may be performed using any method.

At operation 606, the data processing system determines which of a plurality of disease-associated variants are pharmacomimetic instruments for the disease of interest. A disease-associated variant can be a pharmacomimetic instrument if the disease-associated variant modulates a function or expression of a target gene of a drug such that a first effect of the disease-associated variant on a phenotype is likely to be predictive of a second effect of the drug on the phenotype.

To determine which of the plurality of disease-associated variants are pharmacomimetic instruments for the disease of interest, the data processing system may execute a program (e.g., GCTA COJO-SLCT) for the disease of interest to identify "conditionally independent disease-associated variants."

For example, groups of genetic variants that are close together on a DNA molecule (e.g., roughly within 500,000 base pairs) can be inherited together. Variants that are usually inherited together are said to be in "linkage disequilibrium". When a single variant contributes to the risk of a disease, a GWAS will reveal statistical associations of that variant (the "causal variant") with the disease, but also statistical associations with the disease for other variants that are in linkage disequilibrium (inherited together) with the causal variant. Therefore, in GWAS, when there is a group of variants that are close together in their position on a DNA molecule, and many of those variants are associated with the disease, the data processing system can distinguish between two scenarios: 1) a scenario in which all of the apparent disease-associated variants are inherited together, which would imply that there is likely to be a single "causal variant", or 2) a scenario in which there are two or more distinct groups of variants, with one or more variants in each group, such that variants within each group are inherited together, but the inheritance of one group vs. another is independent. In this latter case, there is likely to be one "causal variant" per group of linked variants.

To distinguish between the "single causal variant" and the "multiple causal variants" scenario, the data processing system can implement a regression function. For example, first, a GWAS (e.g., a first GWAS) can be performed as normal. The data processing system can identify the variant that has the most significant association with the disease outcome (e.g., the smallest p-value) across the whole genome. The data processing system can rerun the GWAS, this time conditioning all of the variant-disease association tests on the genotype of the most-significant variant. The data processing system can identify the variant that has the next-most significant association with the disease outcome. The data processing system can rerun the GWAS, this time conditioning all of the variant-disease association tests on the genotype of the most-significant and the 2nd-most-significant variants. The data processing system can iteratively repeat this procedure until determining no variant is associated with the disease below a defined p-value threshold (e.g., a genome-wide significance threshold, such as $5\times10^{-8}$). Using lower thresholds can reduce the chances that an analytical result is a fluke, but increases the chance that the data processing will not identify an important variant, and vice versa. The data processing system can use any threshold. Responsive to stopping the procedure, the set of variants the data processing system identified can be called "conditionally-independent disease-associated variants" because each variant is associated with the disease even after conditioning on the genotypes of all of the previous variants.

Returning to the "single causal variant" and "multiple causal variants" scenarios, if the data processing system identified only a single "conditionally-independent disease-associated variant" in a given region of DNA during the stepwise regression, then the "single causal variant" scenario is more likely to be true. However, if the stepwise regression identified several "conditionally-independent disease-associated variants", then the "multiple causal variants" scenario is more likely to be true.

In instances in which a disease (e.g., coronary artery disease) is associated with multiple biomarkers (e.g., LDL cholesterol and blood pressure), the data processing system may use multiple independent acceptance criteria to identify biomarker-associated variants to increase the number of variants that the data processing system identifies. For example, the data processing system can identify variants with $p<5\times10^{-8}$ for the disease and variants with $p<5\times10^{-6}$ for the disease that also have $p<5\times10^{-8}$ for at least one disease-relevant biomarker. The data processing system can use any criteria to identify variants. The variations in acceptance criteria can enable the data processing system to identify a wide range of variants using a COJO-SLCT analysis.

The data processing system can create a table. Each row of this table can correspond to one subject from the study cohort. The columns of the table are described as follows:

a. Whether the subject is a case or control for the disease. Cases are assigned a value of "1" and controls are assigned a value of "0". Subjects who are neither cases nor controls are excluded from the table.
  b. Age and sex of the subject.
  c. The PCs of genetic ancestry from the operation 602 or 604.
  d. The scaled PGS for disease risk from the operation 604.
  e. The subject's dosage for the alternate allele of each of the independent disease-associated variants.
     i. Here, "alternate allele" is in reference to a reference genome such as the Genome Reference Consortium's GRCh37 or GRCh38. In a reference genome, each variant has a "reference allele". A bi-allelic variant is therefore a site in the genome where an individual has either the "reference allele" or an "alternate allele" at the site.
     ii. Some sites are "multi-allelic", meaning that in the population, three or more alleles exist. Computationally, each alternate allele is treated as a separate bi-allelic variant, (e.g., if you have alleles "reference", "alternate-1", and "alternate-2", then it would be treated as two bi-allelic variants (reference, alternate-1) and (reference, alternate-2)).

The data processing system can identify which of the disease-associated variants are "pharmacomimetic instruments" (e.g., variants that modulate the function or expression of a drug target gene so that the variants' effect on human phenotypes is likely to be predictive of the drug's effect on human phenotypes). Depending on the configuration, the data processing system can use different criteria and/or priorities to identify pharmacomimetic instruments from the identified disease-associated variants. In one example, a user may be interested in clinical-stage drugs for the disease. In this case, the data processing system can compile a table of clinical-stage drugs and their targets using public resources, such as clinicaltrials.gov, and/or proprietary databases, such as Cortellis. The data processing system can determine the variants that are close to a drug target gene (e.g., within 150 kb of the gene's transcription start site) or that are mapped to the drug target are pharmacomimetic instruments. In another example, a user may be interested in known and novel drug targets for the antibody modality. In this case, the data processing system can compile a list of genes that encode proteins that are druggable with the antibody modality (e.g., proteins that are secreted or localized to the cell surface). The data processing system can determine variants that are mapped to an antibody-druggable protein are pharmacomimetic instruments. The data processing system can determine variants that are mapped to an antibody-druggable protein are pharmacomimetic instruments based on the compiled table (e.g., based on the determined variants having stored associations with the antibody-druggable protein).

Optionally, one might require that genetic evidence support the hypothesis that inhibition of the target would be beneficial, as opposed to activation of the target. This evaluation could consider data from expression quantitative trait locus (eQTL) and protein quantitative trait locus (pQTL) datasets that inform on how genetically-determined changes in expression of the target affect disease risk.

In some embodiments, there is more than one suitable variant for a drug mechanism. In this case, the data processing system can increase statistical power to detect drug-PGS interactions by aggregating variants (e.g., all of the variants) identified as pharmacomimetic instruments that were associated with a given drug mechanism into a combined allelic score. To do so, for example, the data processing system can compute an allelic score in the same or a similar manner to a PGS (e.g., assign each variant a weight and compute, for each subject in the cohort, the sum over each variant of (the variant's weight)*(the subject's dosage for the variant)). The difference between an allelic score and a PGS is that the allelic score is composed of variants that modulate the function or expression of a single drug target gene, while a PGS can be composed of variants across the genome that affect many different genes. The variants in the allelic score may be weighted using a GWAS (e.g., a second GWAS) for the disease that did not include any subjects from the study cohort. Alternatively, the variants can be weighted using a GWAS (e.g., a third GWAS) for a biomarker that causally mediates the effect of the drug target on the disease (e.g., LDL cholesterol mediates the effect of PCSK9 on coronary artery disease). A biomarker GWAS still must not overlap the study cohort. The allelic score can be used in place in of PGS to perform the systems and methods described herein.

At operation 608, the data processing system determines statistical interactions between the pharmacomimetic instruments for one or more drug targets and the biomarker stratifier scores. The statistical interactions can be predictive of drug target-specific differential treatment responses for the disease of interest. To determine the statistical interactions, the data processing system can generate a data table with phenotypes (e.g., nonalcoholic steatohepatitis (NASH), coronary heart disease, dry age-related macular degeneration, rheumatoid arthritis, atopic disease, obesity, etc.), covariates, and a set of pharmacomimetic instruments determined using the aforementioned systems and methods, which may include single variants and multi-variant allelic scores. Responsive to doing so, the data processing system can test for interactions between the pharmacomimetic instruments and the PGS (or allelic scores) in association analysis with the disease or risk factor trait of interest.

For example, for each pharmacomimetic instrument, the data processing system can use statistical software, such as the R programming language, to fit a logistic regression model using the following example formula: disease case-control status~age+sex+ancestry PCs+(pharmacomimetic instrument)+(scaled PGS)+(pharmacomimetic instrument): (scaled PGS). The model can be implemented using the R programming language, such as by using the command glm(model_formula, family="binomial", data=our_genetic_and_phenotypic_data). In the example formula, the variable to the left of the symbol is the dependent variable (e.g., the variable that is being predicted). Each of the variables to the right of the "~" symbol, separated by "+" symbols, are independent variables, (e.g., variables that are observed in the data and used to predict the dependent variable). The ":" symbol indicates a variable that is the product (result of multiplication) of the variables to the left and right of the ":" symbol. This product is an "interaction term". If the pharmacomimetic instrument:scaled polygenic score (PGS) interaction term—one of the independent variables—has a statistically-significant association with the dependent variable (in this case, disease status), controlling for all of the other independent variables—such as age and sex—then the data processing system can predict or determine that the drug that is modeled by the pharmacomimetic instrument will have different effects in subjects with high PGS vs. low PGS. The data processing system can fit a logistic regression model for each pharmacomimetic instrument that the data processing system determines or identifies, such as based on the PGS of the different subjects.

The data processing system can use the same program to compute a p-value for the interaction term. If the p-value for the interaction between a pharmacomimetic instrument and the PGS is <0.05/(the # of instruments tested), the data processing system can determine the interaction to be "Bonferroni significant." Alternatively, the data processing system can be configured to use a more lenient p-value threshold, at the risk of false positives.

The instrument-PGS interactions can be "drug-PGS interactions" because each pharmacomimetic instrument is a model for a particular drug mechanism.

The data processing system can generate tables that present the statistically significant drug-PGS interactions in a way that is easier to interpret than looking at the raw regression model outputs. For example, first, the data processing system can group the subjects of the study cohort by quantiles of the PGS, (e.g., the 0-33rd percentile, the 34th-66th percentile, and the 67th-100th percentile). Then, for each drug-PGS interaction, the data processing system can fit separate logistic regression models within each PGS quantile using the formula: disease case-control status~age+sex+ancestry PCs+the pharmacomimetic instrument for the drug. Using these regression outputs, the data processing system can construct a table that shows the effect of the pharmacomimetic instrument on disease risk (as well as a 95% confidence interval for that effect) within each PGS quantile.

For instance, the data processing system can divide the subjects of the study into a finite number of groups (e.g., the groups) based on their PGS values. Within each group, the data processing system can predict a disease outcome based on the patients' genetics, specifically a genetic instrument that mimics the effects of a drug (the "pharmacomimetic instrument"). In doing so, the data processing system can determine a difference in how strongly the pharmacomimetic instrument predicts the disease outcome in individuals with high PGS vs. middle PGS vs. low PGS. The difference may indicate that a drug might have different efficacy in people with high PGS vs. middle PGS vs. low PGS.

The data processing system can also compute a statistic called the "treatment effect multiplier." This is the effect of the pharmacomimetic instrument on disease risk in the top quartile divided by the effect in all subjects. The "treatment effect multiplier" can represent how much one could increase the average treatment effect in a clinical trial of the drug if one enrolled only patients in the top quartile of the PGS as opposed to enrolling all qualified patients. The treatment effect multiplier is a way to compare drug-PGS interactions to distinguish "strong" from "weak" interactions.

At operation 610, the data processing system performs one or more prediction-based actions. The data processing system can perform the one or more prediction-based actions based on the determined interactions. The one or more prediction-based actions can include at least one of (i) therapeutic development, (ii) therapeutic target identification, or (iii) pharmacogenomics. To perform a prediction-based action, the data processing system can select a patient for treatment. The data processing system can select the patient based on a likelihood that the patient will benefit from the treatment. For example, the data processing system can select the patient by determining a PGS for the patient using the systems and methods described herein and determining the PGS for the patient is above a threshold (e.g., a PGS threshold) or within a range (e.g., a quartile, a quintile, a defined range, etc.). In another example, the data processing system can select patients for novel therapeutic mechanisms whose benefit is mostly or only apparent in subsets of common disease patients who have elevated polygenic risk. This enables novel target identification and novel therapeutic discovery. This application can be called "polygenic therapeutic target ID." In another example, the data processing system can select patients from large common disease treatment-eligible populations who will benefit most from existing drug therapies, and, conversely, identify patients who are not likely to receive clinically meaningful benefit. This can enhance the pharmaco-economic profile of existing therapeutic mechanisms, yielding more cost-effective utilization. This can be called "polygenic pharmacogenomics." In another example, the data processing system can select mechanisms and design of prospective clinical trials of investigational drugs that are predicted to yield greater benefit in individuals with elevated PGS. These trials may be run with many-fold fewer patient years required to demonstrate clinical benefit, given the expectation of magnified event rate and treatment response rates. This application can be called "polygenic therapeutic development." In some embodiments, the injections, therapy, and/or treatment techniques can be performed on the selected individuals when performing the one or more prediction-based actions.

In one example, the systems and methods described herein can be used to treat a patient. For instance, a patient can visit a clinic. The clinician can collect a blood sample, a saliva sample, or a tissue sample from the patient. The clinician can use the collected sample to perform a genotyping array on the patient. A data processing system implementing the systems and methods described herein can analyze the patient's genetic data to generate principal components (PCs) that reflect the patient's genetic ancestry. The patient can undergo tests to identify relevant biomarkers for a disease of interest (e.g., diabetes, cancer, cardiovascular diseases, psychiatric disorders, autoimmune diseases, neurological disorders, infectious diseases, asthma and allergies, etc.). These biomarkers are quantifiable biological parameters that could include patient characteristics such as blood sugar levels, cholesterol levels, specific protein markers, etc., depending on the disease. The data processing system can calculate a biomarker stratifier score for the patient for a disease of interest (e.g., a disease of interest from the list above) based on the results from the biomarker tests and the genetic ancestry data (e.g., the PCs).

The data processing system can scan the patient's genetic data for disease-associated variants. In doing so, the data processing system can identify genes or gene variants in the patient's genetic data that are associated with the disease for which the data processing system determined the biomarker stratifier score for the patient. For instance, the data processing system can identify disease-associated variants for the disease using the systems and methods described herein. The data processing system can use the identified disease-associated variants as a key in a query through the genetic array data of the patient. Based on the query, the data processing system can identify any disease-associated variants in the patient's genetic data.

The data processing system can determine which of the identified disease-associated variants are pharmacomimetic instruments (e.g., whether these genetic variants can predict how the patient might respond to certain drugs or methods of treatment). For example, prior to determining treatment for the patient, the data processing system may have identified a list of pharmacomimetic instruments for the disease of interest using the systems and methods described herein. The data processing system can compare the identified disease-associated variants in the patient's genetic makeup with the list of pharmacomimetic instruments. Based on the comparison, the data processing system can identify a set of pharmacomimetic instruments of the patient. In some embodiments, the data processing system can identify the pharmacomimetic instruments of the patient by querying the patient's genetic data for instances of the pharmacomimetic instruments for the disease without identifying the disease-associated variants.

The data processing system can determine one or more treatments for the patient based on the pharmacomimetic instruments and the biomarker stratifier score of the patient. The data processing system can do so, for example, based on statistical interactions that the data processing system has previously determined for the pharmacomimetic instruments and biomarker stratifier scores. For instance, the data processing system can store a record (e.g., a record based on logistic regressions of PGS or biomarker stratifier scores and the pharmacomimetic instruments) indicating that individuals with a high polygenic risk score or biomarker stratifier score (e.g., above a threshold) for the disease of interest may have a high positive response to a therapeutic inhibitor (represented by a pharmacomimetic instrument) and individuals with a low polygenic risk score or biomarker stratifier score (e.g., below the threshold) for the disease of interest may have a low positive response to the inhibitor. The patient may have a high polygenic risk score or biomarker stratifier score. Accordingly, the data processing system can generate a record (e.g., a file, notification, alert, user interface, data structure, etc.) indicating or recommending to treat the patient with a therapeutic inhibitor. The data processing system can display the record on a user interface of a client device accessed by the clinician. The data processing system can recommend any form of treatment based on interactions between pharmacomimetic instruments and polygenic risk scores biomarker stratifier scores of patients.

The clinician can treat the patient based on the recommendation. For example, the clinician can view the recommendation to use the inhibitor to treat the patient. The clinician can administer the treatment, such as by administering pills or capsules, administering an injection or set of injections, or using gene editing tools. The clinician can perform any type of treatment based on the polygenic risk scores or biomarker stratifier scores, type of disease, and/or pharmacomimetic instruments of the patient.

In some embodiments, the data processing system can automatically perform a treatment (e.g., using a gene editing tool or another treatment device or mechanism) responsive to determining the treatment. For example, the data processing system can determine a treatment to inhibit a particular gene to treat a disease for a patient as described herein. The data processing system can configure a treatment machine (e.g., a gene editing tool) to automatically implement the treatment on the patient responsive to the determination, such as by controlling the machine to perform the treatment (e.g., inhibiting or otherwise editing a specific gene or by performing an injection).

In another example, the systems and methods described herein can be used to perform a clinical trial to determine the efficacy of a candidate drug. For instance, the data processing system can identify a disease of interest that the candidate drug is intended to treat. The data processing system can identify pharmacomimetic instruments for the disease of interest. The data processing system can identify a pharmacomimetic instrument for the candidate drug, such as based on a user input. The data processing system can receive genetic data of a study cohort. The data processing system can determine polygenic risk scores for the study cohort using the systems and methods described herein based on the genetic data.

The data processing system can select participants for the trial based on the polygenic risk scores and interaction data between the polygenic risk scores and the pharmacomimetic instrument for the candidate drug. For instance, the data processing system can identify interactions between the pharmacomimetic instrument and the polygenic risk scores. From the identified interactions, the data processing system can determine that there is a high positive interaction between high polygenic risk scores (e.g., polygenic risk scores that exceed a threshold) and the pharmacomimetic instrument. Accordingly, the data processing system may filter participants from the study cohort and identify participants for the study cohort that have a high polygenic risk score. The data processing system can generate a record including the list of patients identified for the trial. The data processing system can present the list of patients on a user interface to a clinician and/or perform treatment on the participants in the trial as described above.

Figure 7:
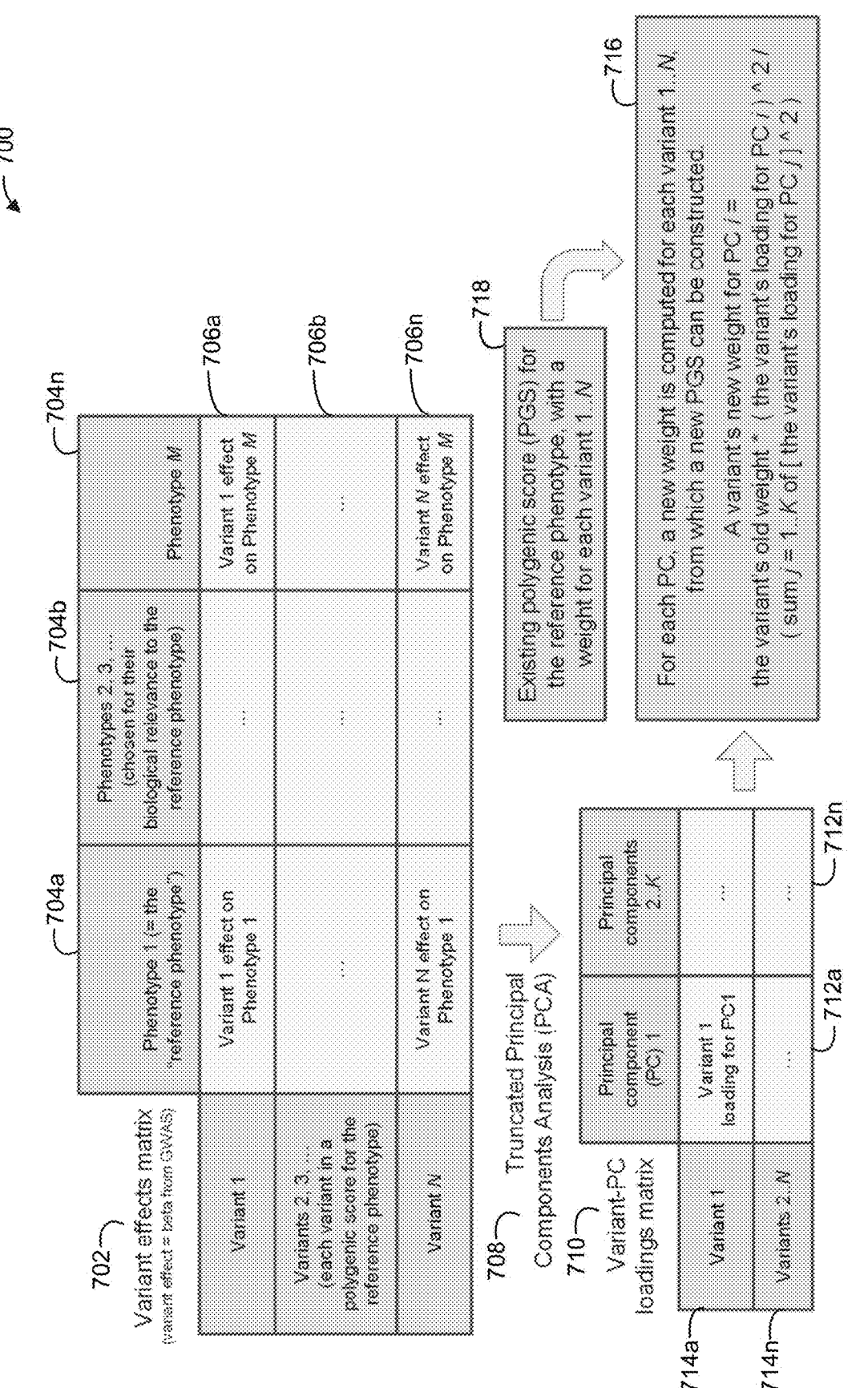
FIG. 7 illustrates a sequence for in silico drug development and determination of drug activity in one embodiment of the disclosure.

FIG. 7 illustrates a sequence 700 for in silico drug development and determination of drug activity in one embodiment of the disclosure. The sequence 700 includes an illustrations of matrices that can be used in performing the systems and methods described herein. A data processing system (e.g., a client device or the data processing system 302, shown and described with reference to FIG. 3, a server system, etc.) can perform the operations and generate the matrices of the sequence 700. The sequence 700 may include more or fewer operations and the operations may be performed in any order. Performance of the method 700 may enable the data processing system to automatically determine interactions between pharmacomimetic instruments and perform prediction-based actions based on the determined interactions.

For example, the data processing system performing the sequence 700 can generate a variant effects matrix 702. The data processing system can generate the variant effects matrix 702 to have columns 704a-n (columns 704) and rows 706a-n (rows 706). n can be any number and can vary between the columns 704 and the rows 706. The columns 704 can each correspond to a different phenotype. In some embodiments, the column 704a can correspond to a reference phenotype and the columns 704b-n can be phenotypes that are biologically relevant to the reference phenotype of the column 704a. The rows 706 can each correspond to variant effects of separate variants on the phenotypes of the respective columns 704. The data processing system can determine the values for the variant effects and insert the values into the variant effects matrix 702.

The data processing system can perform a truncated principal components analysis (PCA) 708 on the variant effects matrix 702 to generate a variant-PC loadings matrix 710. The data processing system can generate the variant-PC loadings matrix 710 to have columns 712a-n (columns 712) and rows 714a-n (rows 714). The columns 712 can each correspond to a different principal component. The rows 706 can each correspond to a different variant. The values in the intersections between the columns 712 and the rows 714 can indicate variant loads for particular principal components.

The data processing system can generate or calculate a weight (e.g., a new weight) for each PC and variant combination 716. The data processing system can use the weight to generate a new PGS for the phenotypes. The data processing system can do so using the following equation: A variant's new weight for $PC_i$=the variant's old weight*(the variant's loading for $PC_i)^2$/(sum$_j$=1 . . . k of [the variant's loading for $PC_j]^2$). The variant's old weight can be the weight for the variant that was used to determine an existing PGS 718. The data processing system can use the newly calculated weights to calculate PGSs for phenotypes using the systems and methods described herein. The data processing system can use PGSs to identify patients for treatment and/or entities may treat patients based on the PGSs.

Variant Data for Polygenic Scores

There are many possible approaches to combine information across loci for assessment of polygenic risk scores (PRSs) for various conditions. Many studies have shown that PRSs can predict disease status in research-based case-control studies. See, e.g., Mavaddat N, et al., Am J Hum Genet. 2019; 104:21-34 Wray N Ret al., Nat Genet. 2018; 50:668-81. More convincingly, the prediction is also valid in population-based cohort studies and in electronic health record-based studies, especially for psychiatric disorders. Musliner K L et al. JAMA Psychiatry. 2019; 76:516-25; Lewis C M and Hagenaars S P, JAMA Psychiatry. 2019; 76:470-2; Zheutlin A B, et al., Am J Psychiatry. 2019,176 (10):846-55. The PRS can be formed from a set of independent risk variants associated with a disorder, based on the current evidence from the largest or most informative genome-wide association studies. For each individual, the number of risk alleles carried at each variant (0, 1, or 2) is summed, weighted by its effect size (i.e., log (OR) for binary traits or beta coefficient for continuous traits). The outcome is a single score of each individual's genetic loading for a disease or for a continuous trait.

Much of the research on polygenic scores comes from research studies in cardiovascular disease, type 2 diabetes, breast and prostate cancers, and Alzheimer's disease (Lambert S A et al. Hum Mol Genet. 2019:28(R2): R133-42). Studies using the UK Biobank have demonstrated that PRS based on variant data can identify which percentage of patients have at least 3-fold increased risk for coronary artery disease, atrial fibrillation, type 2 diabetes, inflammatory bowel disease, and breast cancer, with the proportion of individuals identified varying between 15 and 8% depending on the disorder, Khera A V et al, Nat Genet. 2018: 50:1219-24. Although these effects appear modest, PRS can identify substantial larger fractions of the population at high disease risk than monogenic mutations, making PRS potentially more clinically relevant.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting of" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "coronary artery disease," "coronary heart disease" or "CAD" refer to heart conditions caused by reduced blood flow to the heart, resulting in a reduction of oxygen and nutrients to the heart muscle. Medical manifestations of this condition include, but are not limited to, angina, myocardial infarction and coronary revascularization.

The term "in silico modeling" refers to use of computational models to predict drug effects and/or health outcomes in different scenarios.

"Molecular stratified biomarker data" includes at a minimum one of the following types of data: genomic, transcriptomic, metabolomic, or proteomic. These data are obtained by assays specific to each biomarker type.

Disease phenotypes are based on knowledge of a patient's disease status (e.g., whether a patient has been diagnosed with CAD, yes/no) at a given point in time. Disease phenotypes may also include quantitative disease traits (e.g., LDL, HDL, and Tg measurements at a given time with respect to disease diagnosis), medication information (e.g., patient has taken or is taking a statin or other lipid-lowering therapy at a given time with respect to disease outcomes), and demographic information (e.g., age at diagnosis, biological sex, etc.).

As used herein, a "biological pathway" refers to (1) a bespoke set of genes for which their protein products are known to interact in a biological pathway (e.g., complement pathway, JAK/STAT pathway, MAPK pathway, etc.), or (2) an unsupervised learning approach (e.g., principal component analysis (PCA)) that yields patterns in the data such that clusters of genes comprising a pathway may be identified. In some embodiments, approach (1) is based on canonical pathways identified by literature and external pathway databases, while approach (2) is a data-driven analysis that results in identification of pathways.

As used herein, "biological pathway activity" is defined by information form the literature or external databases that provide evidence for gene or protein expression indicative of pathway activity (e.g., 'up regulation' or 'down regulation' of pathway X in disease Y).

As used herein, a "drug target expression" refers to a protein expression as measured in participants of a large cohort (e.g., UK Biobank), where the protein analyzed is a known drug target or is a target that may be druggable (even if not already drugged). In some embodiments, a biomarker stratifier score (e.g., a polygenic score, a proteomics score, a transcriptomics score, or a somatic mutation score) for "a drug target expression" is computed same as it would be for any other quantitative trait, where the outcome of the model is a quantitative measurement.

As used herein, a "disease outcome" refers to a clinical event that is the result of having a disease. For example, coronary artery disease (CAD) or atherosclerotic cardiovascular disease (ASCVD) are diseases, but a myocardial infarction or stroke are events that occur in patients with ASCVD/CAD and are therefore 'disease outcomes.'

As used herein, the term "drug target" refers to any gene or gene product (e.g., RNA or polypeptide) with implications in an associated disease or disorder. Non-limiting examples include various proteins such as enzymes, oncogenes and their polypeptide products, and cell cycle regulatory genes and their polypeptide products.

As used herein, the phrase "external data" refers to data from an independent set of individuals or population, unused in molecular biomarker stratifier data score determination. In some embodiments, external data is used to assess the predictive power of the methods described herein. In some embodiments, external data is used to prevent overfitting during molecular biomarker stratifier data score determination. At a minimum, the external data is from a large cohort of participants of an observational study (e.g., UK Biobank or eMERGE). In some embodiments, the external data is divided into training and validation subsets. In some embodiments, estimates of biomarker effect are validated in multiple studies, which may include both observational studies and health system patient cohorts.

As used herein, the phrase "genetic variant" refers to an alteration, variant or polymorphism in a nucleic acid sample or genome of a subject. Such alteration, variant or polymorphism can be with respect to a reference genome, which may be a reference genome of the species (e.g., for human, hG19 or hG38), the subject or other individual. Variations include one or more single nucleotide variations (SNVs), insertions, deletions, repeats, small insertions, small deletions, small repeats, structural variant junctions, variable length tandem repeats, and/or flanking sequences, copy number variants (CNVs), transversions, gene fusions and other rearrangements are also forms of genetic variation. A variation can be a single nucleotide variation (SNV), insertion or deletion (indel), repeat, copy number variation (CNV), transversion, or a combination thereof.

As used herein, "a genome-wide association study" (GWA study, or GWAS), refers to an observational study of a genome-wide set of genetic variants in different individuals to see if any variant is associated with a trait. In some embodiments, a GWAS study focuses on associations between gene variants (e.g., single-nucleotide polymorphisms (SNPs)) and phenotypic traits (e.g., diseases). In some embodiments, a genetic variant is a somatic genetic variant. In some embodiments, a genetic variant is a germline genetic variant.

In some embodiments, GWA studies compare the DNA of participants having varying phenotypes for a particular trait or disease. These participants may be people with a disease (cases) and similar people without the disease (controls), or they may be people with different phenotypes for a particular trait, for example blood pressure. This approach is known as phenotype-first, in which the participants are classified first by their clinical manifestation(s), as opposed to genotype-first. Each person gives a sample of DNA, from which millions of genetic variants are determined (e.g., using SNP arrays or sequencing). If there is significant statistical evidence that one type of the variant (one allele) is more frequent in people with the disease, the variant is said to be associated with the disease. The associated SNPs are then considered to mark a region of the human genome that may influence the risk of disease.

As used herein, the phrase "molecular biomarker stratifier" or "biomarker stratifier" refers to a molecular marker that is different between two distinct states (e.g., healthy versus diseased).

As used herein, the phrase "molecular biomarker stratifier distribution" or "biomarker stratifier distribution" refers to a subset of data obtained from individual-level cohort data (e.g., data from UK Biobank), where subsets may be defined as the top 10%, 20%, 30%, etc. of the distribution. The threshold that is chosen to define a subset of a molecular biomarker stratifier distribution will depend on the use case. For example, it may be optimal to use a 25th percentile of the coronary heart disease molecular biomarker stratifier score (e.g., a polygenic score) to define a subset of patients who are predicted to have an outsized clinical benefit from a given therapy. Alternatively, a 33th percentile of the coronary heart disease molecular biomarker stratifier score may be used to define a subset of patients who would benefit most from a second, different given therapy. In other disease settings with different molecular biomarker stratifier scores, the thresholds may also vary. Defining the optimal threshold will depend on factors such as: estimated effect size for the subset vs. all-corners on therapy, and screen failure rate (a "screen failure" is candidate who undergoes screening—meaning they are checked for eligibility—but who does not meet the clinical trial's inclusion/exclusion criteria in a trial.

A "screen failure rate" refers to the number of ineligible candidates divided by the number of screened candidates). If the threshold is set too conservatively, e.g., 5%, a lot more patients will have to be screened to enroll a few eligible candidates.

As used herein, the phrase "molecular biomarker stratifier effect" or "biomarker stratifier effect" refers to an estimated magnitude of the effect of a biomarker on disease risk or continuous disease trait from a statistical model.

As used herein, the phrase "molecular biomarker stratifier score" or "biomarker stratifier score" refers to a score that is cumulative of data from across a plurality (hundreds, thousands, tens of thousands or more) of possible biomarker stratifiers that could be used to predict an individual's risk for an illness. In some embodiments, a statistical model is trained using summary statistics from a published study on large-scale cohorts or from a meta-analysis of multiple studies based on large and diverse set of cohorts. Then, the estimated weights from that model are applied to a dataset that is orthogonal to the ones used for training (e.g., UK Biobank). For example, a Bayesian high-dimensional linear regression model for a set of populations may be used, where body mass index (BMI) is the dependent variable, and a genome-wide set of SNPs and their effect sizes from a published study of BMI from the GIANT Consortium (Locke et al. 2015) serve as inputs. Population-specific reference panels (e.g., 1000 Genomes) are used to infer linkage disequilibrium, and population-specific PRS are derived. A linear regression of the normalized PRS for each population is then fit, and can be applied to the individual-level genotype and phenotype data in the UK Biobank.

In some embodiments, molecular biomarker stratifier comprises, or alternatively consists essentially of, or yet further consists of a genetic variant and the biomarker stratifier score comprises, or alternatively consists essentially of, or yet further consists of a polygenic score.

In some embodiments, molecular biomarker stratifier comprises, or alternatively consists essentially of, or yet further consists of a proteomic variant and the biomarker stratifier score comprises, or alternatively consists essentially of, or yet further consists of a proteomics score.

In some embodiments, molecular biomarker stratifier comprises, or alternatively consists essentially of, or yet further consists of a transcriptional variant and the biomarker stratifier score comprises, or alternatively consists essentially of, or yet further consists of a transcriptomics risk score.

In some embodiments, molecular biomarker stratifier comprises, or alternatively consists essentially of, or yet further consists of a somatic mutational variant and the biomarker stratifier score comprises, or alternatively consists essentially of, or yet further consists of a somatic mutational risk score.

As used herein, the term "pharmacomimetic" refers to showing a similar response or a similar lack of a response to a therapeutic agent or a class of therapeutic agents.

As used herein, the phrase "pharmacomimetic variant interaction" refers to a plurality of biomarker stratifiers that in combination correlate with showing a similar response or a similar lack of a response to a therapeutic agent or a class of therapeutic agents.

As used herein, the phrase "pharmacomimetic instruments" refers to biomarker stratifiers that modulate function or expression of a drug target gene so that the biomarker stratifiers' effect on human phenotypes is likely to be predictive of the drug's effect on human phenotypes.

As used herein, a "pharmacomimetic genetic score" is a score that indicates the likelihood of a patient to respond to a particular drug or a particular class of drugs. In some embodiments, for a given gene, more than one pharmacomimetic variant (defined as a functional variant in gene that is strongly and significantly associated with a given disease) may be identified. Instead of analyzing the variants of this gene separately, their effects are combined as a "pharmacomimetic genetic score."

As used herein, the phrase "polygenic score" or "polygenic risk score" or "PGS" or "PRS" refers to a metric that summarizes the estimated effect of many genetic variants on an individual's phenotype, typically calculated as a weighted sum of trait-associated alleles. In some embodiments, a polygenic score reflects an individual's estimated genetic predisposition for a given trait and can be used as a predictor for that trait. In some embodiments, a polygenic score gives an estimate of how likely an individual is to have a given trait only based on genetics, without taking environmental factors into account.

As used herein, the phrase "proteomics score" refers to a metric that summarizes the estimated effect of many differences in the protein composition (e.g., differences in the amount of proteins, mutational variants of proteins; post-translational modification of proteins) on an individual's phenotype, typically calculated as a weighted sum of trait-associated differences. In some embodiments, a proteomics score can be used as a predictor for a given trait. In some embodiments, a proteomics score is used to identify patients most likely to receive an outsized benefit from a particular therapy. In some embodiments, a protein composition of a subject is determined by mass spectroscopy. In some embodiments, a "proteomics score" is estimated from a regression model, e.g., least absolute shrinkage and selection operator (LASSO) (which implements variable selection and regularization for optimal prediction accuracy) for protein measurements vs. outcome, followed by cross-validation procedures.

As used herein, the phrase "transcriptomics score" refers to a metric that summarizes the estimated effect of many differences in the RNA transcript composition on an individual's phenotype, typically calculated as a weighted sum of trait-associated differences. In some embodiments, a transcriptomics score refers to a linear or non-linear combination of transcript abundance values that associate with a disease or clinical phenotype. In some embodiments, a transcriptomics score can be used as a predictor for a given trait. In some embodiments, an RNA transcript composition of a subject is determined by RNA-seq, or microarray.

As used herein, the phrase "somatic mutational risk score" refers to a metric that summarizes the estimated effect of somatic mutations on an individual's phenotype, typically calculated as a weighted sum of trait-associated somatic mutations. In some embodiments, a somatic mutational risk score can be used as a predictor for a given trait. In some embodiments, an somatic mutational composition of a subject is determined by next generation (high-throughput) sequencing.

As used herein, the phrase "Principal Component Analysis" (PCA) refers to a technique for analyzing large datasets containing a high number of dimensions/features per observation, increasing the interpretability of data while preserving the maximum amount of information, and enabling the visualization of multidimensional data. In some embodiments, PCA refers to a statistical technique for reducing the dimensionality of a dataset. In some embodiments, reduction the dimensionality is accomplished by linearly transforming the data into a new coordinate system where the variation in the data can be described with fewer dimensions than the initial data. As used herein, "principal components" are a set of new variables that are combinations of the original variables in the original large datasets.

As used herein, a "statistical interaction" refers to the coefficient of a predictor defined by the product of the pharmacomimetic genetic score and biomarker score in a regression model to predict a phenotype relevant to the drug indication. Specifically, if the p-value for a test of the hypothesis that the coefficient for this PGS-biomarker product term is non-zero is statistically significant ($p<0.05$ or $p<0.05/\#$ of tests performed if multiple hypotheses are tested), then the PGS and biomarker are considered to have a "statistical interaction". If the sign of the coefficient for the PGS-biomarker product term is the same as the sign of the marginal biomarker term, that indicates that the predictive and/or causal effects of the biomarker on the phenotype are amplified in subjects with high PGS.

As used herein an "association analysis" refers to a process of searching for hidden association or pattern in a large dataset. In some embodiments, an association analysis is carried out using a statistical model such as linear regression, logistic regression, or Cox Proportional Hazards model, e.g. where the dependent variable is a clinical trait or disease phenotype assessed at a single time point, or censored survival time to disease onset or event, and the independent variables include weighted effects of biomarker stratifiers, demographic information, and other clinical features.

As used herein, a "phenotype intermediate" refers to a demonstration of partial or incomplete dominance between two or more genes (e.g., two alleles may produce an intermediate phenotype when both are present, rather than one fully determining the phenotype).

As used herein, the term "HSD17B13" refers to "Hydroxysteroid 17-Beta Dehydrogenase 13" enzyme (UniProtKB/Swiss-Prot: Q7Z5P4). A pharmacomimetic genetic score "associated with a response to a drug that targets HSD17B13" is used to determine whether the subject will respond to an HSD17B13 inhibitor (e.g., BI-3231 as described in Thamm, Sven, et al., Journal of Medicinal Chemistry 66.4 (2023): 2832-2850, which is incorporated herein in its entirety).

As used herein, "LPL" refers to Lipoprotein Lipase enzyme (UniProtKB/Swiss-Prot: P06858), "ANGPTL3" refers to the Angiopoietin-like 3 protein (UniProtKB/Swiss-Prot: Q9Y5C1), and "ANGPTL4" refers to the Angiopoietin-like 4 protein (UniProtKB/Swiss-Prot: Q9BY76). A subject having a pharmacomimetic genetic score "associated with a response to a drug that targets LPL/ANGPTL4/ANGPTL3" is expected to respond to an LPL agonist, an ANGPTL4 inhibitor and/or an ANGPTL3 inhibitor.

As used herein, "C3" refers to Complement C3 protein (UniProtKB/Swiss-Prot: P01024). A pharmacomimetic genetic score "associated with a response to a drug that targets C3" is used to determine whether the subject will respond to a C3 inhibitor.

As used herein, "CFB" refers to Complement Factor B protein (UniProtKB/Swiss-Prot: P00751). A pharmacomimetic genetic score "associated with a response to a drug that targets CFB" is used to determine whether the subject will respond to a CFB inhibitor.

As used herein, "CFH" refers to Complement Factor H protein (UniProtKB/Swiss-Prot: P08603). A pharmacomimetic genetic score "associated with a response to a drug that targets CFH" is used to determine whether the subject will respond to a CFB inhibitor.

As used herein, "HTRA1" refers to HtrA Serine Peptidase 1 protein (UniProtKB/Swiss-Prot: Q92743). A pharmacomimetic genetic score "associated with a response to a drug that targets "HTRA1" is used to determine whether the subject will respond to a HTRA1 inhibitor.

As used herein, "TYK2" refers to the "Tyrosine Kinase 2" enzyme (UniProtKB/Swiss-Prot: P29597). A pharmacomimetic genetic score "associated with a response to a drug that targets TYK2" is used to determine whether the subject will respond to a TYK2 inhibitor.

As used herein, "IL33" refers to "Interleukin 33" (UniProtKB/Swiss-Prot: O95760). As used herein, "TSLP" refers to "Thymic Stromal Lymphopoietin" (UniProtKB/Swiss-Prot: Q969D9). As used herein, "IL4R" refers to "Interleukin 4 Receptor" (UniProtKB/Swiss-Prot: P24394). A pharmacomimetic genetic score "associated with a response to a drug that targets IL33/TSLP/IL4R" is used to determine whether the subject will respond to a IL33/TSLP/IL4R inhibitor, e.g., bispecific antibodies targeting IL33/TSLP/IL4R. As used herein, "GLP1R" refers to "Glucagon Like Peptide 1 Receptor" (UniProtKB/Swiss-Prot: P43220). As used herein, "GIPR" refers to "Gastric Inhibitory Polypeptide Receptor" (UniProtKB/Swiss-Prot: P48546). A pharmacomimetic genetic score "associated with a response to a drug that targets GLP1R/GIPR" is used to determine whether the subject will respond to a GLP1R and/or GIPR agonist.

Systems of the Disclosure for Risk Score-Informed Drug Development

There are many applications of the systems of the present disclosure, ranging from drug discovery using agnostic analysis of new chemical entities in combination with genetic variant distribution in patient populations, to new and efficient designs of clinical trials, to incorporation of new end points in clinical trials, to how the data from former clinical studies are analyzed to provide evidence of effectiveness. Applications of particular value include combining genetic information on patient populations with a better understanding of pharmacodynamic end points and biomarkers and how they relate to clinical outcomes.

For example, the systems of the disclosure can be used for in silico clinical trial recapitulation and regulatory evaluation. Historically, safety and efficacy data provided to regulatory agencies in support of marketing has required preclinical and clinical efficacy data using empirical methods.

Therapeutic Areas

The systems of the disclosure can be used for drug development in various therapeutic areas, including but not limited to autoimmune diseases; cardiovascular diseases such as CAD; dental and oral health; dermatology; endocrinology; gastroenterology; orphan genetic diseases; hematology; hepatology; immunology; infectious diseases; metabolic disorders; musculoskeletal disorders; nephrology; neurology, including neurodegenerative disease; obstetrics/gynecology; oncology; ophthalmology; orthopedics; otolaryngology; psychiatric disorders; pulmonary/respiratory diseases; rheumatology; and urology.

Exemplary therapeutic indications within certain therapeutic areas that can be addressed using the drug development systems of the disclosure include, but are not limited to, those shown in Table 1:

TABLE 1

| Therapeutic Areas and Indications | |
| --- | --- |
| Therapeutic Area | Indications |
| Autoimmune | Addison disease |
| | Celiac disease |
| | Crohn's disease |
| | Dermatomyositis |
| | Graves' disease |
| | Hashimoto thyroiditis |
| | Inflammatory bowel disease |
| | Multiple sclerosis |
| | Myasthenia Gravis |
| | Pernicious anemia |
| | Plaque psoriasis |
| | Reactive arthritis |
| | Rheumatoid arthritis |
| | Sjogren's syndrome |
| | Systemic lupus erythematosus |
| | Type I diabetes |
| Cardiovascular | Atherosclerosis |
| | Atrial fibrillation |
| | Coronary artery disease |
| | Congestive heart failure |
| | Dilated Cardiomyopathy (DCM) and symptomatic chronic heart failure |
| | Hypertrophic cardiomyopathy |
| | Hypertension |
| | Pulmonary hypertension |
| | Raynaud's Phenomenon |
| | Tachyarrhythmia |
| Dermatology | Alopecia areata |
| | Aphthous ulcer |
| | Candidiasis (cutaneous, oropharyngeal) |
| | Cystic acne |
| | Dermatosis (steroid-responsive dermatosis) |
| | Idiopathic urticaria |
| Endocrinology/ Metabolism | Hypercholesterolemia |
| | Hyperparathyroidism |
| | Obesity |
| | Type II Diabetes Mellitus |
| Gastroenterology | Gastroesophageal Reflux Disease (GERD) |
| | Irritable Bowel Syndrome (IBS) |
| | Nephropathic cystinosis |
| | Non-alcoholic steatohepatitis (NASH) |
| | Ulcerative Colitis (UC) |
| Hematology | Thrombocythemia |
| | Thrombocytopenia |
| | Thromboembolism |
| Neurology | Alzheimer's disease |
| | Epilepsy |
| | Frontotemporal dementia |
| | Migraine |
| | Narcolepsy |
| | Obsessive-Compulsive Disorder |
| | Parkinson's disease |
| Oncology | Bladder Cancer |
| | Breast Cancer |
| | Colorectal Cancer |
| | Endometrial Cancer |
| | Kidney Cancer |
| | Leukemia |
| | Liver Cancer |
| | Lung Cancer |
| | Melanoma |
| | Non-Hodgkin Lymphoma |
| | Ovarian cancer |
| | Pancreatic Cancer |
| | Prostate Cancer |
| | Thyroid Cancer |
| Ophthalmology | Glaucoma |
| | Age-related Macular degeneration |
| Psychiatric | Attention deficit hyperactivity disorder (ADHD) |
| | Autism and Autism Spectrum Disorder |
| | Bipolar disorder |
| | Depression/Major Depressive Disorder (MDD) |
| | General Anxiety Disorder (GAD) |
| | Obsessive compulsive disorder (OCD) |

TABLE 1-continued

| Therapeutic Areas and Indications | |
| --- | --- |
| Therapeutic Area | Indications |
| | Panic disorder |
| | Schizophrenia |
| | Tourette's syndrome |
| Pulmonary | Allergic Rhinitis |
| | Asthma |
| | Bronchopulmonary dysplasia |
| | Fibromyalgia |
| Renal disease | Chronic kidney disease (CKD) |
| | End stage renal disease |
| | Hyponatremia |
| Rheumatology | Juvenile Idiopathic Arthritis (JIA) |
| | Juvenile Rheumatoid Arthritis (JRA) |
| | Polyarticular Juvenile Idiopathic Arthritis (PJIA) |

The present approach may be configured as a system or method, but also may be provided as a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions and/or steps specified in the disclosure. These computer readable program instructions may also be stored in a computer readable storage medium that can direct a computer, a programmable data processing apparatus, and/or other devices to function in a particular manner, such that the computer readable storage medium having instructions stored therein comprises, or alternatively consists essentially of, or yet further consists of an article of manufacture including instructions which implement aspects of the functions and/or steps specified in the disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions and/or steps specified in the disclosure.

Methods for Determining Drug Activity

An aspect of the disclosure is directed to an in silico method for determining drug activity of a plurality of drug targets, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

Nonalcoholic steatohepatitis (NASH): Another aspect of the disclosure is directed to an in silico method for determining drug activity of a plurality of drug targets associated with nonalcoholic steatohepatitis (NASH), the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype for NASH comprises, or alternatively consists essentially of, or yet further consists of one or more of a quantitative disease trait (e.g., a blood marker), medication information, demographic information (e.g., age at diagnosis, biological sex), itchy skin, abdominal swelling (also called ascites), shortness of breath, swelling of the legs, spider-like blood vessels just beneath the skin's surface, enlarged spleen, red palms, or yellowing of the skin and eyes (jaundice).

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

In some embodiments, the biomarker stratifier score is a fatty liver polygenic score.

In some embodiments, the plurality of drug targets is associated with nonalcoholic steatohepatitis (NASH), and the plurality of drug targets comprises, or alternatively consists essentially of, or yet further consists of HSD17B13.

In some embodiments, the pharmacomimetic genetic score is associated with a response to a drug that targets HSD17B13.

In some embodiments, the drug that targets HSD17B13 is a HSD17B13 inhibitor.

Coronary Heart Disease: Another aspect of the disclosure is directed to an in silico method for determining drug activity of a plurality of drug targets associated with coronary heart disease, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype comprises, or alternatively consists essentially of, or yet further consists of one or more of a quantitative disease trait (e.g., LDL level, HDL level, triglyceride level), medication information, demographic information (e.g., age at diagnosis, biological sex), chest pain (angina), shortness of breath, fatigue, heart attack, nausea, sweating, fatigue, faster heartbeat, weakness, or dizziness.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

In some embodiments, the plurality of drug targets is associated with coronary heart disease, and the plurality of drug targets comprises, or alternatively consists essentially of, or yet further consists of LPL, ANGPTL4 and/or ANGPTL3.

In some embodiments, the pharmacomimetic genetic score is associated with a response to a drug that targets LPL, ANGPTL4 and/or ANGPTL3. In some embodiments, the drug a LPL, ANGPTL4 and/or ANGPTL3inhibitor.

Dry Age-Related Macular Degeneration: Another aspect of the disclosure is directed to an in silico method for determining drug activity of a plurality of drug targets associated with dry age-related macular degeneration, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype comprises, or alternatively consists essentially of, or yet further consists of one or more of blurry or blind spot in central vision in one or both eyes, difficulty recognizing faces or reading words, reduced light intensity or color brightness, visual distortions, such as seeing bent lines on straight objects, or increased difficulty adapting to low light levels.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

In some embodiments, the plurality of drug targets is associated with dry age-related macular degeneration, and the plurality of drug targets comprises, or alternatively consists essentially of, or yet further consists of C3, CFB, CFH, and/or HTRA1.

In some embodiments, the pharmacomimetic genetic score is associated with a response to a drug that targets C3, CFB, CFH, and/or HTRA1. In some embodiments, the drug a C3, CFB, CFH, and/or HTRA1 inhibitor.

Rheumatoid Arthritis: Another aspect of the disclosure is directed to an in silico method for determining drug activity of a plurality of drug targets associated with rheumatoid arthritis, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype comprises, or alternatively consists essentially of, or yet further consists of one or more of swollen joints, accumulation of fluid in the ankles, morning stiffness, joint pain, fatigue, joint redness, increased eye sensitivity and dryness, mouth dryness, nodules on the skin, or inflammation of the lungs.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the plurality of drug targets is associated with rheumatoid arthritis, and the plurality of drug targets comprises, or alternatively consists essentially of, or yet further consists of TYK2.

In some embodiments, the pharmacomimetic genetic score is associated with a response to a drug that targets TYK2. In some embodiments, the drug a TYK2 inhibitor.

Atopic Disease: Another aspect of the disclosure is directed to an in silico method for determining drug activity of a plurality of drug targets associated with atopic disease, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype comprises, or alternatively consists essentially of, or yet further consists of one or more of dry skin, itching, swelling and inflammation, red, brown, purple or gray rashes, small, fluid-filled bumps or crusting, cracked skin, Rash, skin creasing on the palms of the hand or under the eye, or darkening of skin around the eyes.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the plurality of drug targets is associated with atopic disease, and the plurality of drug targets comprises, or alternatively consists essentially of, or yet further consists of IL33, TSLP and/or IL4R.

In some embodiments, the pharmacomimetic genetic score is associated with a response to a drug that targets IL33, TSLP and/or IL4R. In some embodiments, the drug a IL33, TSLP and/or IL4R inhibitor.

Obesity: Another aspect of the disclosure is directed to an in silico method for determining drug activity of a plurality of drug targets associated with obesity, the method comprising, or alternatively consisting essentially of, or yet further consisting of: obtaining molecular biomarker stratifier data comprising, or alternatively consisting essentially of, or yet further consisting of a plurality of biomarker stratifiers and at least one disease phenotype from each of a plurality of subjects; determining a plurality of values representing biomarker stratifier effects, wherein each value separately represents how each of the plurality of biomarker stratifiers affects each of the at least one disease phenotype based on external data; calculating a biomarker stratifier score for a chosen disease phenotype; calculating a pharmacomimetic genetic score for each drug target; and identifying the predicted drug activity of each drug target the at least one disease phenotype in subsets of the biomarker stratifier distribution based on the statistical interaction of the biomarker stratifier score with the pharmacomimetic genetic score for each drug target in association analysis with the disease phenotype.

In some embodiments, a disease phenotype comprises, or alternatively consists essentially of, or yet further consists of one or more of body mass index (BMI) of over 30, sleep apnea, varicose veins, skin problems caused by moisture that accumulates in the folds of the skin, gallstones, or osteoarthritis.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomic s score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the plurality of drug targets is associated with obesity, and the plurality of drug targets comprises, or alternatively consists essentially of, or yet further consists of GLP1R and/or GIPR.

In some embodiments, the pharmacomimetic genetic score is associated with a response to a drug that targets GLP1R and/or GIPR. In some embodiments, the drug a GLP1R and/or GIPR agonist.

In some embodiments, the polygenic score is a body mass index polygenic score.

Another aspect of the disclosure is directed to an in silico method for determining drug activity of a plurality of drug targets, the method comprising:

obtaining molecular biomarker stratifier data and at least one disease phenotype from each of a plurality of subjects;

determining the value of the biomarker stratifier effects for each disease phenotype based on external data;

constructing a matrix based on the biomarker stratifiers, disease phenotypes and values;

running a principal components analysis biomarker stratifier x phenotype-related phenotype biomarker stratifier effects matrix;

calculating a biomarker stratifier score for each principal component;

calculating a pharmacomimetic genetic score for each drug target; and identifying predicted drug activity of each drug target on one or more phenotypes in subsets of the biomarker stratifier distribution based on the statistical interaction of the polygenic score calculated for each principal component with the pharmacomimetic genetic score for each drug target in association analysis with the outcome phenotype.

Another aspect of the disclosure is directed to an in silico method for determining the drug activity of drug targets on a plurality of phenotype intermediates, comprising:

obtaining molecular biomarker stratifier data and disease phenotypes from each of a plurality of subjects;

determining the value of the biomarker stratifier effects for each phenotype intermediate based on external data;

calculating a biomarker stratifier score for each phenotype intermediate in the disease process;

calculating a pharmacomimetic genetic score for each drug target on each phenotype intermediate; and identifying predicted drug activity of the drug targets on one or more phenotypes in subsets of the biomarker stratifier distribution based on the statistical interaction of the biomarker stratifier score with the pharmacomimetic genetic score for each drug target in association analysis with the phenotype intermediate and the outcome phenotype.

Another aspect of the disclosure is directed to method of determining the drug activity of a drug target, comprising:

obtaining molecular biomarker stratifier data and disease phenotypes from each of a plurality of subjects;

determining the value of the biomarker stratifier effects for each phenotype based on external data;

calculating a biomarker stratifier score for a chosen outcome phenotype related to the disease outcome;

calculating a pharmacomimetic genetic score for the drug target; and identifying predicted drug activity of the drug target on one or more phenotypes in subsets of the biomarker stratifier distribution based on the statistical interaction of the biomarker stratifier score with the pharmacomimetic genetic score for the drug target in association analysis with the outcome phenotype.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

In some embodiments, the method further comprises, or alternatively consists essentially of, or yet further consists of running a principal components analysis (PCA) or a weighted principal components analysis (wPCA) to identify one or more principal components for one or more of the biomarker stratifier effects.

In some embodiments, the method further comprises, or alternatively consists essentially of, or yet further consists of running the principal components analysis or the weighted principal component analysis based on a matrix of one or more of the biomarker stratifier effects.

In some embodiments, the method further comprises, or alternatively consists essentially of, or yet further consists of constructing the matrix based on one or more of the biomarker stratifiers, the phenotypes, and the plurality of values.

In some embodiments, the method further comprises, or alternatively consists essentially of, or yet further consists of adjusting the genetic score for each drug target and the biomarker stratifier score for each of the principal components.

In some embodiments, the weighted principal component analysis is performed according to the biomarker stratifier score of the chosen disease phenotype.

In some embodiments, the method further comprises, or alternatively consists essentially of, or yet further consists of the weighted principal component analysis identifies predicted drug activity of the plurality of drug targets for the at least one disease phenotype.

Another aspect of the disclosure is directed to an in silico method comprising:

generating a plurality of principal components (PCs) corresponding to genetic ancestry data for subjects in a study cohort;
  generating a biomarker stratifier score for each subject in the study cohort based at least on (i) the PCs and on (ii) biomarker stratifier weights for a disease of interest;
  determining which of a plurality of disease-associated variants are pharmacomimetic instruments for the disease of interest, where a disease-associated variant is a pharmacomimetic instrument if the disease-associated variant modulates a function or expression of a target gene of a drug such that a first effect of the disease-associated variant on a phenotype is likely to be predictive of a second effect of the drug on the phenotype;
  determining statistical interactions between the pharmacomimetic instruments for one or more drug targets and the biomarker stratifier scores, wherein the statistical interactions are predictive of drug target-specific differential treatment response for the disease of interest; and
  performing one or more prediction-based actions based on the determined interactions.

In some embodiments, the one or more prediction-based actions comprises at least one of (i) therapeutic development, (ii) therapeutic target identification, or (iii) pharmacogenomics.

In some embodiments, the genetic ancestry data indicates whether subjects in the study cohort are a case or a control for the disease of interest.

In some embodiments, the genetic ancestry data is based on genotyping arrays or whole-genome sequencing.

In some embodiments, the genetic ancestry data is obtained from a publicly-available database.

In some embodiments, the plurality of PCs comprises at least 5 PCs.

In some embodiments, the study cohort comprises at least 200 control subjects.

In some embodiments, each disease-associated variant in the plurality of disease-associated variants satisfies a genome-wide significance threshold.

In some embodiments, the plurality of disease-associated variants is determined based on a first disease genome-wide association study (GWAS).

In some embodiments, the biomarker stratifier score for each subject is a scaled biomarker stratifier score.

In some embodiments, the scaled biomarker stratifier score is based at least on a raw PGS and an ancestry-normalized PGS.

In some embodiments, the PGS variant weights are computed independent of the genetic ancestry data corresponding to the study cohort.

In some embodiments, determining which of the plurality of disease-associated variants are pharmacomimetic instruments for the disease of interest comprises generating an allelic score.

In some embodiments, variants in the allelic score are weighted based at least on a second GWAS that did not include any of the subjects in the study cohort.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

Systems

Another aspect of the disclosure is directed to an in silico system for drug development, such system comprising: at least one hardware processor; and a non-transitory computer-readable storage medium having stored thereon program code, the program code executable by the at least one hardware processor to:

obtain molecular biomarker stratifier data and disease phenotypes from each of a plurality of subjects;

determine the value of the biomarker stratifier effects for each phenotype based on external data;

construct a matrix based on the biomarker stratifiers, phenotypes and values;

run a principal components analysis biomarker stratifier x phenotype-related phenotype biomarker stratifier effects matrix;

calculate a biomarker stratifier score for each principal component;

calculate a pharmacomimetic genetic score for each drug target;

identify predicted drug effects on one or more phenotypes in subsets of the biomarker stratifier distribution based on the statistical interaction of the polygenic score calculated for each principal component with the pharmacomimetic genetic score for each drug target in association analysis with the outcome phenotype.

In some embodiments, the biomarker stratifier comprises, or alternatively consists essentially of, or yet further consists of a genetic variant and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression, or any linear or non-linear combination thereof.

In some embodiments, the biomarker stratifier comprises, or alternatively consists essentially of, or yet further consists of a proteomic variant, and wherein the biomarker stratifier score comprises, or alternatively consists essentially of, or yet further consists of one or more score selected from: (i) a proteomics score for a disease phenotype; (ii) a proteomics score for a disease risk factor; (iii) a proteomics score for a biological pathway activity; (iv) a proteomics score for a drug target expression; or any linear or non-linear combination thereof.

In some embodiments, the biomarker stratifier comprises, or alternatively consists essentially of, or yet further consists of a transcriptional variant, and wherein the biomarker stratifier score comprises, or alternatively consists essentially of, or yet further consists of one or more score selected from: (i) a transcriptomics score for a disease phenotype; (ii) a transcriptomics score for a disease risk factor; (iii) a transcriptomics score for a biological pathway activity; or any linear or non-linear combination thereof.

In some embodiments, the biomarker stratifier comprises, or alternatively consists essentially of, or yet further consists of a somatic mutational variant, and wherein the biomarker stratifier score comprises, or alternatively consists essentially of, or yet further consists of one or more score selected from: (i) a somatic mutation score for a drug target expression; (ii) a somatic mutation score for a disease phenotype; (iii) a somatic mutation score for a disease risk factor; (iv) a somatic mutation score for a biological pathway activity; (v) a somatic mutation score for a drug target expression; or any linear or non-linear combination thereof.

In some embodiments, the biomarker stratifier comprises, or alternatively consists essentially of, or yet further consists of a genetic variant, a proteomic variant, a transcriptional variant and/or a somatic mutational variant, and wherein the biomarker stratifier score comprises, or alternatively consists essentially of, or yet further consists of one or more score selected from: (i) a polygenic score for a disease phenotype; (ii) a polygenic score for a disease risk factor; (iii) a polygenic score for a biological pathway activity; (iv) a polygenic score for a drug target expression; (v) a proteomics score for a disease phenotype; (vi) a proteomics score for a disease risk factor; (vii) a proteomics score for a biological pathway activity; (viii) a proteomics score for a biological pathway activity; (ix) a proteomics score for a drug target expression; (x) a transcriptomics score for a disease phenotype; (xi) a transcriptomics score for a disease risk factor; (xii) a transcriptomics score for a biological pathway activity; (xiii) a somatic mutation score for a drug target expression; (xiv) a somatic mutation score for a disease phenotype; (xv) a somatic mutation score for a disease risk factor; (xvi) a somatic mutation score for a biological pathway activity; (xvii) a somatic mutation score for a drug target expression; or any linear or non-linear combination thereof.

EXAMPLES

The following examples are included for illustrative purposes only and are not intended to limit the scope of the disclosure.

Example 1: Local CAD PRS

In clinical trials of PCSK9 inhibitors for secondary prevention in coronary artery disease (CAD), patients with high PRS for CAD had substantially greater relative risk reduction than patients with low PRS, despite the two groups having similar amounts of LDL cholesterol reduction (Marston et al. 2019, Damask et al. 2019). Similarly, high PRS amplifies the relative risk reduction provided by statins for primary prevention of CAD (Natarajan 2017).

The in silico modeling systems of the present disclosure were able to recapitulate the clinical trial interaction between pharmacological PCSK9 inhibition and PRS observed in clinical trials. The clinical data was replicated in silico using UK Biobank genetic variants. Kheraj A V et al. Nat Genet 2018; 50:1219-24. Cohort information on these subjects and prevalence of CAD is summarized in Table 2.

TABLE 2 summarizes the cohort statistic of patients in the
UK Biobank study (ukbiobank.ac.uk).

| Variable | Not on lipid lowering medication at baseline | On lipid lowering medication at baseline |
|---|---|---|
| # subjects | 294,656 | 63,860 |
| Median age at baseline | 57.0 | 63.0 |

US 12,646,591 B2

59

TABLE 2-continued summarizes the cohort statistic of patients in the
UK Biobank study (ukbiobank.ac.uk).

| Variable | Not on lipid lowering medication at baseline | On lipid lowering medication at baseline |
|---|---|---|
| Median age at death or date of last available data | 69.1 | 74.7 |
| % died during follow-up period | 5.4% | 12.9% |
| % male | 43.0% | 61.7% |
| Median LDL (mg/dl) | 142.4 | 105.8 |
| Median TG (mg/dl) | 128.2 | 151.4 |
| % CAD | 6.4% | 33.6% |

These "pharmacomimetic" variants discovered in silico mimic the effect of a known drug by reducing PCSK9 function. These pharmacomimetic variants in LPL, the target for triglyceride-lowering drugs interact with the in silico PRS to determine the risk of CAD.

rsll591147 (R46L), weight=−0.48 rsll206510 (intergenic), weight=−0.07 rs2479409 (intergenic), weight=−0.047 rs505151 (G670Q), weight=−0.09

A two-gene GRS was also calculated from six pharmacomimetic variants in LPL and ANGPTL4, a protein that physically binds to and inhibits LPL. The variants were weighted by their effect on serum triglycerides in the same study as above (Id.).

rsl3702 (LPL 3' UTR), weight=−0.12 rs328 (LPL S474X), weight=−0.18 rs268 (LPL N318S), weight=0.24 rsl801177 (LPL D36N), weight=0.17 rsll6843064 (ANGPTL4 E40K), weight=−0.27 rs7255436 (ANGPTL4 intron), weight=−0.019

Finally, a two-gene GRS was calculated from two pharmacomimetic variants in the incretin hormone receptors GLP1R and GIPR.

rsl042044 (GLP1R L260F), weight=0.00895 rsl800437 (GIPR E354Q), weight=−0.0283

The GLP1R and GIPR variants were weighted by their effect on body mass index in a manually performed meta-analysis of four BMI GWAS (just for the two variants). None of the GWAS overlap search other or overlap the UK Biobank.

Locke et al. 2015 (GIANT consortium) (Locke, Adam E., et al. "Genetic studies of body mass index yield new insights for obesity biology." Nature 518.7538 (2015): 197-206.)

Sakae et al. 2021 (Biobank Japan) (Sakaue, S., Kanai, M., Tanigawa, Y. et al. A cross-population atlas of genetic associations for 220 human phenotypes. Nat Genet 53, 1415-1424 (2021))

Fernandez-Rhodes et al. 2022 (Hispanic Community Health Study/Study of Latinos) (Fernindez-Rhodes, Lindsay, et al. "Ancestral diversity improves discovery and fine-mapping of genetic loci for anthropometric traits—The Hispanic/Latino Anthropometry Consortium." Human Genetics and Genomics Advances 3.2 (2022))

Wojcik et al. 2019 (PAGE study) (Wojcik, Genevieve L., et al. "Genetic analyses of diverse populations improves discovery for complex traits." Nature 570.7762 (2019): 514-518.)

Example 2: Genome-Wide CAD PRS

A PRS for CAD was developed by applying the program PRS-CS (Ge et al. 2019) to an inverse variance-weighted meta-analysis of two GWAS:

Nikpay et al. 2015=CARDioGRAMplusC4D ("A comprehensive 1000 Genomes-based genome-wide association meta-analysis of coronary artery disease." Nature genetics 47, no. 10 (2015): 1121-1130.)

Kukri=Finnegan release 6, using the phenotype I9_CHD (Kurki, Mitja I., et al. "FinnGen provides genetic insights from a well-phenotyped isolated population." Nature 613.7944 (2023): 508-518.)

These GWAS do not have any overlap with the UK Biobank.

The PRS was selected from one of a set of PRS that was trained using different hyperparameters for PRS-CS. The hyperparameter value was selected that gave the best predictive performance in the UK Biobank, which is the same cohort in which the pharmacomimetic variant x PRS interaction tests were performed. The confounding effect was expected to be minimal, however, because the PRS-CS' only hyperparameter, phi, represents the polygenicity of the disease being studied, and the optimal value for phi should not be dependent on LD structure, which is the main driver of differential performance of PRS across cohorts.

Example 3: Pathway-Specific CAD PRS

A list of 264 conditionally independent variants associated with CAD (p<5e-7) was obtained from van der Harts and Verweij 2017 (Van Der Harst, Pim, and Niek Verweij. "Identification of 64 novel genetic loci provides an expanded view on the genetic architecture of coronary artery disease." Circulation research 122.3 (2018): 433-443). A matrix was constructed where the rows were the CAD variants, the columns were CAD-related phenotypes (including CAD itself), and the values were the variants' effects for each phenotype, sourced from several GWAS listed below.

To select CAD-related phenotypes, the genetic correlation (R 2) between CAD and many candidate phenotypes were computed using the 264 CAD variants. All UK Biobank biomarkers and blood counts, as well as a variety of other CAD-related phenotypes, were also included in the matrix 9 phenotypes that had a genetic correlation R 2 to CAD>=0.25:

CAD itself, R A2=1, (van der Harts P and Verweij N. Circ Res. 2018 Feb. 2; 122(3):433-443).

Abdominal aortic aneurysm, RA 2=0.49, (Zhou Z, et al., Medicine (Baltimore). 2021 Oct. 1; 100(39): e27306.)

Lipoprotein A, RA 2=0.46, UK Biobank

Non-HDL cholesterol, RA 2=0.31, Graham S E et al. Nature. 2021 December; 600(7890):675-679.

Systolic blood pressure, RA 2=0.31, UI<Biobank

Total cholesterol, R A 2=0.30, Graham et al. Supra.

LDL cholesterol, RA 2=0.29, Graham et al. Supra.

Pulse pressure, R A 2=0.28, UK Biobank

Ischemic stroke, R A 2=0.25, Malik et al. 2018

Phenotypes that had R A 2<0.25, and were thus excluded from the matrix, included:

HDL cholesterol

Triglycerides

Diastolic blood pressure

Mean arterial pressure

Body mass index

Type 2 diabetes

HbA1c

C-reactive protein

Applicant ran a principal components analysis (PCA) on the CAD variant x CAD-related phenotype variant effects matrix (e.g. a matrix where the columns represent the CAD risk phenotypes described above [abdominal aortic aneurysm, lipoprotein A, non-HDL cholesterol, systolic blood pressure, total cholesterol, LDL cholesterol, pulse pressure, and ischemic stroke] and the rows represent genetic association weights for each genetic variant position). The estimated percentage of each variants' effect on CAD that was mediated by principal component 1 was defined as (the variant's loading for PC1)2/(sum of the squares of the variants' loadings for all PCs). This was repeated for PCs 2-9.

Based on the trait associations of each PC and the candidate genes for the variants most strongly associated with each PC, it was inferred that PCs 1-3 correspond to particular & distinct CAD-related pathways, based on manual inspection of biological functions of major genetic loadings of each principal component.

A pathway specific PRS was then constructed for each of PC 1-3. Each variant in the original, genome-wide PRS for CAD was assigned to the closest one of the variants that were include in the PCA. PCA variants for which their unscaled PC loading was inconsistent with their effect on CAD were excluded, e.g., if variant X has a loading of 0.5 for PC1, and PC1 is positively correlated with CAD, variant X was expected and required to have an association with increased risk of CAD. Variants that were >500 kb away from all PCA variants were also excluded.

Next, each variants' weight in the PRS, which was originally computed by PRS-CS, was multiplied by the scaled PC loading of the closest PCA variant for the PC of interest. In other words, loci are reweighted based on whether a locus' effect is estimated to be mediated or not mediated by the pathway that a given PC represents. Finally, the PRS was recomputed using the new weights. This gave three new pathway-specific PRS for PCs 1-3 respectively.

Phenotypes

CAD Cases were defined as any subject who has at least one of the following codes: —ICD-10: 120-125—ICD-9: 410, 412, 414—UK Biobank self-report: 1074, 1075—OPCS-4: K40-K46, K49-K50, K75—Any record in the myocardial infarction registry (UKB data field 42000).

Medications

Subjects who self-reported being on lipid lowering medication at the UKB initial assessment visit were excluded from all analyses. Lipid lowering medication has been shown to mitigate polygenic risk, so the medication—PRS interaction could mask potential pharmacomimetic variant—PRS interactions, given that the pharmacomimetic variants used explained a small proportion of lipid trait variation in the population compared to medication.

Using PCA on variant effects for CAD and CAD-related phenotypes allowed the construction of pathway-specific PRS. Two of these PRS (PC1 and PC2) appeared to have no interaction with the LPL pharmacomimetic variants. Adjusting the genome-wide CAD PRS to remove the contribution from PC1 and PC2 gives a slight but significant (p<0.01) improvement in the magnitude of the LPL pharmacomimetic variant x PRS interaction, while at the same time improving PRS sparsity.

PCSK9 GRS×CAD PRS

The PCSK9 GRS has a nominally significant interaction with the CAD PRS (p<0.05), consistent with clinical trial results. The average effect of genetic PCSK9 loss of function in subjects in the top PRS tertile appears to be almost threefold (2.9×) greater than the average effect in subjects in the bottom or middle PRS tertiles.

The CAD PRS was adjusted to remove the contribution of PCSK9 to the PRS (Table 3).

TABLE 3

| is a table summarizing the interaction between the PCSK9 GRS and the CAD PRS in determining the risk of CAD. | | |
| --- | --- | --- |
| Term | OR | P-Value |
| PCSK9 GRS | 0.71 (0.58, 0.87) | 8.3e−04 |
| CAD PRS | 1.39 (1.37, 1.42) | 0.0e+00 |
| PSCK9 GRS:CAD PRS | 0.78 (0.64, 0.95) | 0.014 |

Subjects who are on lipid lowering medication were excluded from the analysis. The PCSK9 GRS is scaled such that 1 unit corresponds to an amount of lifelong LDL lowering equivalent to the LDL lowering of evolocumab in a clinical trial setting, i.e., −1.56 standard deviations. The units of the CAD PRS are standard deviations.

The CAD PRS was adjusted to remove the contribution of PCSK9 to the PRS (Table 4).

TABLE 4

| is a table summarizing the effect of the PCSK9 GRS on the risk of CAD, stratified by quantiles of the CAD PRS. | | | | | |
| --- | --- | --- | --- | --- | --- |
| PRS percentile | OR | P-value | # cases | # controls | Pre-valence |
| 0-33 | 0.86 (0.59, 1.25) | 0.419 | 4941 | 98069 | 4.8% |
| 33-66 | 0.76 (0.54, 1.08) | 0.128 | 6095 | 92727 | 6.2% |
| 67-100 | 0.53 (0.39, 0.73) | 9.2e−05 | 7913 | 84911 | 8.5% |

Subjects who are on lipid lowering medication were excluded from the analysis. The PCSK9 GRS is scaled such that 1 unit corresponds to an amount of lifelong LDL lowering equivalent to the LDL lowering of evolocumab in a clinical trial setting, i.e., −1.56 standard deviations. The units of the CAD PRS are standard deviations.

The CAD PRS was adjusted to remove the contribution of PCSK9 to the PRS (Table 5). Subjects who are on lipid or blood pressure lowering medication were excluded from the analysis. The PCSK9 GRS is scaled such that 1 unit corresponds to an amount of lifelong LDL lowering equivalent to the LDL lowering of evolocumab in a clinical trial setting, i.e., −1.56 standard deviations. The units of the CAD PRS are standard deviations.

TABLE 5

| is a table summarizing the interaction between the PCSK9 GRS and the CAD PRS in determining the risk of CAD. | | |
| --- | --- | --- |
| Term | OR | P-Value |
| PCSK9 GRS | 0.65 (0.51, 0.83) | 5.1e−04 |
| CAD PRS | 1.43 (1.40, 1.45) | 0.0e+00 |
| PSCK9 GRS:CAD PRS | 0.68 (0.53, 0.86) | 1.4e−03 |

The CAD PRS was adjusted to remove the contribution of PCSK9 to the PRS (Table 6). Subjects who are on lipid or blood pressure lowering medication were excluded from the analysis. The PCSK9 GRS is scaled such that 1 unit corresponds to an amount of lifelong LDL lowering equivalent to the LDL lowering of evolocumab in a clinical trial setting, i.e., −1.56 standard deviations. The units of the CAD PRS are standard deviations.

TABLE 6 is a table summarizing the effect of the PCSK9 GRS on the risk of CAD, stratified by quantiles of the CAD PRS.

| PRS percentile | OR | P-value | # cases | # controls | Pre-valence |
|---|---|---|---|---|---|
| 0-33 | 0.89 (0.57, 1.39) | 0.609 | 3547 | 86879 | 3.9% |
| 33-66 | 0.72 (0.48, 1.08) | 0.114 | 4491 | 81258 | 5.2% |
| 67-100 | 0.42 (0.28, 0.61) | 8.3e−06 | 5775 | 73574 | 7.3% |

LPL/ANGPTL4 GRS×CAD PRS

The LPL/ANGPTL4 GRS also has a significant interaction with the CAD PRS (p<0.01). The effect of genetic LPL activation in subjects in the top PRS tertile appears to be about double (2.2×) the average effect in subjects in the bottom or middle PRS tertiles.

The CAD PRS was adjusted to remove the contribution of LPL and ANGPTL4 to the PRS (FIG. 8). Subjects who are on lipid lowering medication were excluded from the analysis. The LPL/ANGPTL4 GRS is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 7 is a table summarizing the interaction between the LPL/ANGPTL4 GRS and the CAD PRS in determining the risk of CAD.

| Term | OR | P-Value |
|---|---|---|
| LPL/ANGPTL4 GRS | 0.89 (0.85, 0.93) | 2.7e−06 |
| CAD PRS | 1.39 (1.37, 1.42) | 0.0e+00 |
| LPL/ANGPTL4 GRS:CAD PRS | 0.93 (0.89, 0.98) | 4.2e−03 |

The CAD PRS was adjusted to remove the contribution of LPL and ANGPTL4 to the PRS (Table 8). Subjects who are on lipid lowering medication, were excluded from the analysis. The LPL/ANGPTL4 GRS is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 8 is a table summarizing the effect of the LPL/ANGPTL4 GRS on the risk of CAD, stratified by quantiles of the CAD PRS.

| PRS percentile | OR | P-value | # cases | # controls | Pre-valence |
|---|---|---|---|---|---|
| 0-33 | 0.94 (0.86, 1.03) | 0.202 | 4937 | 98119 | 4.8% |
| 33-66 | 0.90 (0.82, 0.97) | 9.7e−03 | 6082 | 92703 | 6.2% |
| 67-100 | 0.83 (0.77, 0.89) | 9.3e−07 | 7930 | 84885 | 8.5% |

The CAD PRS was adjusted to remove the contribution of LPL and ANGPTL4 to the PRS (Table 9). Subjects who are on lipid or blood pressure lowering medication were excluded from the analysis. The LPL/ANGPTL4 GRS is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 9 is a table summarizing the interaction between the LPL/ANGPTL4 GRS and the CAD PRS in determining the risk of CAD.

| Term | OR | P-Value |
|---|---|---|
| LPL/ANGPTL4 GRS | 0.88 (0.84, 0.94) | 1.9e−05 |
| CAD PRS | 1.43 (1.40, 1.45) | 0.0e+00 |
| LPL/ANGPTL4 GRS:CAD PRS | 0.91 (0.86, 0.97) | 1.8e−03 |

The CAD PRS was adjusted to remove the contribution of LPL and ANGPTL4 to the PRS (Table 10). Subjects who are on lipid or blood pressure lowering medication were excluded from the analysis. The LPL/ANGPTL4 GRS is sealed such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 10 is a table summarizing the effect of the LPL/ANGPTLA GRS on the risk of CAD, stratified by quantiles of the CAD PRS.

| PRS percentile | OR | P-value | # cases | # controls | Pre-valence |
|---|---|---|---|---|---|
| 0-33 | 0.95 (0.85, 1.06) | 0.354 | 3552 | 86893 | 3.9% |
| 33-66 | 0.91 (0.82, 1.00) | 0.049 | 4465 | 81311 | 5.2% |
| 67-100 | 0.80 (0.73, 0.87) | 2.7e−07 | 5796 | 73507 | 7.3% |

LPL/ANGPTL4 GRS×TG PRS (Excluding Those Loci)

The LPL/ANGPTL4 GRS does not interact with a. triglycerides PRS, indicating that the GRS: CAD PRS interaction is driven by other pathways besides triglyceride metabolism.

The TG PRS was adjusted to remove the contribution of LPL and ANGPTL4 to the PRS (Table 11). The LPL/ANGPTL4 GRS and is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 11 is a table summarizing the interaction of the LPL/ANGPTL4 GRS with a PRS for TG in determining the risk of CAD in subjects not treated with lipid lowering medication.

| Term | OR | P-Value |
|---|---|---|
| LPL/ANGPTL4 GRS | 0.88 (0.84, 0.93) | 2.9e−07 |
| TG PRS | 1.12 (1.10, 1.13) | 1.8e+46 |
| LPL/ANGPTL4 GRS:TG PRS | 1.00 (0.95, 1.05) | 0.925 |

The TG PRS was adjusted to remove the contribution of LPL and ANGPTL4 to the PRS (Table 12).

TABLE 12

| PRS percentile | Odds ratio (95% CI) | P-value | # cases | # controls | Pre-valence |
|---|---|---|---|---|---|
| | is a table summarizing the effect of the LPL/ANGPTL4 GRS (standardized to –0.5 SD TG) on risk of CAD in subjects not treated with lipid-lowering medication, stratified by percentiles of a PRS for TG. | | | | |
| 0-33 | 0.90 (0.82, 0.98) | 0.017 | 5811 | 92407 | 5.9% |
| 33-66 | 0.85 (0.78, 0.92) | 1.2e–04 | 6277 | 91941 | 6.4% |
| 67-100 | 0.90 (0.84, 0.98) | 9.7e–03 | 6861 | 91359 | 7.0% |

LDL PRS x residual CAD PRS

An LDL PRS has a significant interaction with a "residual CAD PRS" that has correlation with the LDL PRS regressed out. The ratio of the interaction effect to the marginal effect is less than half of what was observed when using the PCSK9 GRS instead of the LDL PRS. This tentatively suggests that the PCSK9 GRS: CAD PRS interaction may not be able to be explained by a class-wide effect where all hypothetical LDL-lowering therapies interact with the CAD PRS. There appears to be some uniqueness to PCSK9 (and HMGCR, based on observed statin-PRS interactions). But our confidence intervals are wide due to use excluding subjects on statins from the analysis, so it is hard to be sure.

The LDL PRS is scaled so that 1 unit corresponds to lifelong LDL lowering equivalent to the LDL lowering of evolocumab in a clinical trial setting, i.e., –1.56 standard deviations (Table 13). The outcome phenotype is CAD in subjects not treated with lipid lowering medication.

TABLE 13 is a table summarizing the interaction of an LDL PRS with a PRS for CAD that is conditioned on the LDL PRS in a simple linear regression model.

| Term | OR | P-Value |
|---|---|---|
| LDL PRS scaled to evolocumab effect | 0.64 (0.58, 0.72) | 4.7e–16 |
| Residual CAD PRS (controlled for LDL PRS) | 1.39 (1.37, 1.41) | 0.0e+00 |
| LDL PRS:Residual CAD PRS (controlled for LDL PRS) | 0.86 (0.78, 0.96) | 5.7e–03 |

The effect of an LDL PRS (standardized to –1.56 SD LDL, the effect of evolocumab) on CAD risk in subjects not treated with lipid-lowering medication, stratified by quantiles of a PRS for CAD that is conditioned on the LDL PRS is shown in Table 14.

TABLE 14

| PRS percentile | Odds ratio (95% CI) | P-value | # cases | # controls | Pre-valence |
|---|---|---|---|---|---|
| | is a table summarizing the effect of an LDL PRS (on CAD risk in subjects not treated with lipid-lowering medication. | | | | |
| 0-33 | 0.72 (0.59, 0.89) | 2.2e–03 | 4631 | 93587 | 4.7% |
| 33-66 | 0.67 (0.56, 0.81) | 2.7e–05 | 6012 | 92207 | 6.1% |
| 67-100 | 0.55 (0.47, 0.64) | 1.6e–03 | 8306 | 89913 | 8.5% |

TG PRS x residual CAD PRS

A triglyceride PRS does not interact with a "residual CAD PRS" that has correlation with the triglyceride PRS regressed out. This indicates that the LPL/ANGPTL4 GRS: CAD PRS interaction cannot be explained by a class-wide effect where all hypothetical TG-lowering therapies interact with the CAD PRS.

The TG PRS is scaled such that 1 unit corresponds to an amount of lifelong TG lowering equal to 0.5 standard deviations=1.67 times the effect of Vascepa (ethyl eicosapentaenoic acid) in a clinical trial setting (Table 15).

TABLE 15 is a table summarizing the outcome phenotype is CAD in subjects not treated with lipid lowering medication.

| Term | OR | P-Value |
|---|---|---|
| TG PRS scaled to –0.5 SD TG | 0.81 (0.79, 0.83) | 9.2e–52 |
| Residual CAD PRS (controlled for TG PRS) | 1.38 (1.36, 1.40) | 0.0e+00 |
| TG PRS:Residual CAD PRS (controlled for TG PRS) | 0.99 (0.97, 1.02) | 0.651 |

The effect of a TG PRS (standardized to –0.5 SD TG) on CAD risk in subjects not treated with lipid-lowering medication, stratified by quantiles of a PRS for CAD that is conditioned on the TG PRS is shown in Table 16.

TABLE 16

| PRS percentile | Odds ratio (95% CI) | P-value | # cases | # controls | Pre-valence |
|---|---|---|---|---|---|
| | is a table summarizing the effect of a TG PRS on CAD risk in subjects not treated with lipid-lowering medication. | | | | |
| 0-33 | 0.81 (0.77, 0.85) | 9.7e–15 | 4726 | 93492 | 4.8% |
| 33-66 | 0.82 (0.78, 0.86) | 1.2e–15 | 5962 | 92257 | 6.1% |
| 67-100 | 0.80 (0.77, 0.83) | 1.7e–26 | 8261 | 89958 | 8.4% |

GLP1R/GIPR GRS x CAD PRS

The association of the GLP1R/GIPR GRS with CAD was not observed, either by itself or in interaction with the CAD PRS.

Subjects who are on lipid lowering medication were excluded from the analysis. The interaction between the GLP1R/GIPR GRS and the CAD PRS (with the contribution of the GLP1R/GIPR GRS regressed out) in determining the risk of CAD is shown in Table 17. The units of the GLP1R/GIPR GRS and the CAD PRS are standard deviations.

TABLE 17 is a table summarizing the interaction between the GLP1R/GIPR GRS and the CAD PRS in determining the risk of CAD.

| Term | OR | P-Value |
|---|---|---|
| GLP1R/GIPR GRS | 1.00 (0.99, 1.02) | 0.734 |
| CAD PRS | 1.40 (1.37, 1.42) | 0.0e+00 |
| GLP1R/GIPR GRS:CAD PRS | 0.99 (0.97, 1.00) | 0.060 |

PCSK9, LPL GRS x PCA-derived, pathway-specific CAD PRS

The LPL/ANGPTL4 pharmacomimetic GRS appears to not interact at all with PRS derived from PC1 or PC2 of our PCA of variant effects on CAD-related phenotypes but does interact strongly with a PRS derived from PC3 of the same PCA, and with a "residual PRS" obtained by regressing out the contributions of PC1, PC2, and PC3 from the genome-wide CAD PRS. To assess the significance of this result, a likelihood ratio test was performed to assess whether a model of CAD risk that has separate interaction terms for GRS: PC1 PRS, GRS: PC2 PRS, GRS: PC3 PRS, and GRS: residual CAD PRS produced a better fit than a model in which all of those four GRS: PRS interaction terms were constrained to be equal. The likelihood ratio test was significant (p<0.01).

The variants with the highest positive loadings for PC1 are all at the LPA locus, suggesting that this PC is associated with Lipoprotein(a) levels. Variants with high positive loadings for PC2 increase LDL cholesterol and CAD risk, and fall in loci containing many canonical regulators of LDL, such as HMGCR, PCSK9, and LDLR. Variants with high positive loadings for PC3 increased risk of CAD and abdominal aortic aneurysm without having substantial effects on lipids. Manual review of the loci containing these variants suggests that PC3 is related to vascular smooth muscle cell and/or vascular endothelial cell function.

No specificity was seen with the interactions of the PCSK9 GRS with the PCA-derived PRS.

All PRS have been adjusted via linear regression to remove the correlation of the GRS with the PRS. The "Residual CAD PRS" has been further adjusted to remove the correlation of the PC1/2/3 PRS with the genome wide CAD PRS (Table 18). The units of each PRS are standard deviations. The GRS is scaled to match expected drug effects (–1.56 SD of LDL for the PCSK9 GRS, –0.5 SD of TG for the LPL/ANGPTL4 GRS). Likelihood ratio test Table 18: is a table summarizing the interaction between the PCSK9 GRS and several PCA-derived CAD PRS in a joint model of CAD risk in subjects who have not been treated with lipid-lowering medication.

| Term | OR | P-Value |
|---|---|---|
| PCSK9 GRS | 0.91 (0.67, 1.24) | 0.540 |
| CAD PC1 PRS (Lp(a) associated genes) | 1.12 (1.10, 1.14) | 9.9e–32 |
| CAD PC2 PRS (LDL associated genes) | 1.10 (1.08, 1.12) | 2.5e–19 |
| CAD PC3 PRS (vascular function genes) | 1.16 (1.14 1.18) | 4.1e–46 |
| Residual CAD PRS | 1.26 (1.24, 1.28) | 3.7e–148 |
| PCSK9 GRS:CAD PCI PRS (Lp(a) associated genes) | 0.88 (0.68, 1.14) | 0.322 |
| PCSK9 GRS:CAD PC2 PRS (LDL associated genes) | 0.90 (0.71, 1.15) | 0.400 |
| PCSK9 GRS:CAD PC3 PRS (vascular function genes) | 0.73 (0.56, 0.96) | 0.023 |
| PCSK9 GRS:Residual CAD PRS | 0.94 (0.74, 1.19) | 0.596 |

Model 1: cad~age_atright_censoring+age_at_right_censoring_sq+sex+uk_bileve+PC1+pc2+pc3+pc4+pc5+pc6+grs*(cad_PC1_lpa_prs+cad_pc2_ldl_prs+cad_pc3_vascular_prs+resid-ual_cad_prs) Model 2: cad-age_atright_censoring+age_at_right_censoring_sq+sex+uk_bileve+PC1+pc2+pc3+pc4+pc5+pc6+grs+cad_PC1_lpa_prs+cad_pc2_1dl_prs+cad_pc3_vascular_prs+residual_cad_prs+grs:I(cad_PC1_lpa_prs+cad_pc2_ldl_prs+cad_pc3_vascular_prs+resid-ual_cad_prs) #Df LogLik Df Chisq Pr(>Chisq)

All PRS have been adjusted via linear regression to remove the correlation of the GRS with the PRS. The "Residual CAD PRS" has been further adjusted to remove the correlation of the PC1/2/3 PRS with the genome-wide CAD PRS (Table 19). The units of each PRS are standard deviations. The GRS is scaled to match expected drug effects (–1.56 SD of LDL for the PCSK9 GRS, –0.5 SD of TG for the LPL/ANGPTL4 GRS).

Likelihood Ratio Test

TABLE 19 is a table summarizing the interaction between the LPL/ANGPTL4 GRS and several PCA-derived CAD PRS in a joint model of CAD risk in subjects who have not been treated with lipid-lowering medication.

| Term | OR | P-Value |
|---|---|---|
| LPL/A GPTL4 GRS | 0.93 (0.88, 0.99) | 0.017 |
| CAD PC1 PRS (Lp(a) associated genes) | 1.12 (1.10, 1.14) | 1.1e–31 |
| CAD PC2 PRS (LDL associated genes) | 1.10 (1.08, 1.12) | 2.9e–20 |
| CAD PC3 PRS ( vascular function genes) | 1.16 (1.14, 1.18) | 1.7e–46 |
| Residual CAD PRS | 1.26 (1.24, 1.28) | 1.0e–147 |
| LPL/ANGPTL4 GRS:CAD PCI PRS (Lp(a) associated genes) | 1.00 (0.94, 1.06) | 0.909 |
| LPL/ANGPTL4 GRS:CAD PC2 PRS (LDL associated genes) | 1.06 (1.00, 1.13) | 0.059 |
| LPL/ANGPTL4 GRS:CAD PC3 PRS (vascular function genes) | 0.90 (0.85, 0.96) | 1.7e–03 |
| LPL/ANGPTL4 GRS:Residual CAD PRS | 0.92 (0.87, 0.98) | 5.5e–03 |

Model 1: cad~age_at_right_censoring+age_at_right_censoring_sq+sex+uk_bileve+pc1+pc2+pc3+pc4+pc5+pc6+grs*(cad_pc1_lpa_prs+cad_pc2_ldl_prs+cad_pc3_vascular_prs+resid-ual_cad_prs) Model 2: cad~age_at_right_censoring+age_at_right_censoring_sq+sex+uk_bileve+pc1+pc2+pc3+pc4+pc5+pc6+grs+cad_pc1_lpa_prs+cad_pc2_ldl_prs+cad_pc3_vascular_prs+residua.l_cad_prs+grs:I(cad_pc1_lpa_prs+cad_pc2_ldl_prs+cad_pc3_vascular_prs+residual_cad_prs) 2 17–50193–3 13.924 0.003011 ** –Signif. codes: 0 "O. 001 "0. 01 "0.05 '.' 0.1 " 1

Regressing out the contribution of PC1 and PC2 from the genome-wide CAD PRS gives an adjusted CAD PRS. This adjusted CAD PRS does slightly better than the unadjusted genome-wide CAD PRS at predicting subjects' response to the LPL/ANGPTL4 pharmacomimetic GRS, despite the adjusted PRS having a marginal effect on CAD that is only 73% of the marginal effect of the genome-wide PRS on CAD. Essentially, a more parsimonious PRS can be constructed that has at least non-inferior performance to the default PRS when applied to study this drug mechanism.

The CAD PRS has been adjusted to remove the contribution of PC1, PC2, LPL, and ANGPTL4 to the PRS (Table 20).

TABLE 20 is a table summarizing the interaction between the LPL/ANGPTL4 GRS and the CAD PRS in determining the risk of CAD.

| Term | OR | P-Value |
|---|---|---|
| LPL/ANGPTL4 GRS | 0.89 (0.84, 0.94) | 2.3e–05 |
| Adjusted CAD PRS | 1.30 (1.27, 1.32) | 2.0e–184 |
| LPL/ANGPTL4 GRS:Adjusted CAD PRS | 0.90 (0.85, 0.95) | 9.9e–05 |

Subjects who are on lipid or blood pres-sure lowering medication were excluded from the analysis. The LPL/ANGPTL4 GRS is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

The CAD PRS has been adjusted to remove the contribution of PC1, PC2, LPL, and ANGPTL4 to the PRS (Table 21). Subjects who are on lipid or blood pressure lowering medication were excluded from the analysis. The LPL/ANGPTL4 GRS is scaled such that 1 unit corresponds to an amount of lifelong TG lowering equal to 0.5 standard deviations=1.67 times the effect of Vascepa (ethyl eicosapentaenoic acid) in a clinical trial setting. The units of the PRS are standard deviations.

TABLE 21 is a table summarizing the effect of the LPL/ANGPTLA GRS on the risk of CAD, stratified by quantiles of the CAD PRS.

| PRS percentile | OR | P-value | # cases | # controls | Pre-valence |
|---|---|---|---|---|---|
| 0-33 | 0.95 (0.85, 1.06) | 0.354 | 3552 | 86893 | 3.9% |
| 33-66 | 0.91 (0.82, 1.00) | 0.049 | 4465 | 81311 | 5.2% |
| 67-100 | 0.80 (0.73, 0.87) | 2.7e-07 | 5796 | 73507 | 7.3% |

Using PCA on variant effects on CAD and CAD-related phenotypes allowed the construction of pathway-specific PRS. Two of these PRS (PC1 and PC2) appeared to have no interaction with the LPL pharmacomimetic variants. Adjusting the genome-wide CAD PRS to remove the contribution from PC1 and PC2 gives a slight but significant (p<0.01) improvement in the magnitude of the LPL pharmacomimetic variant x PRS interaction, while at the same time improving PRS sparsity.

Example 4: Materials and Methods

Phenotypes:
  Coronary artery disease (CAD)
    ICD-10 I20-I25
    ICD-9 410, 412, 414; exclude controls with 411, 413
    Self-reported myocardial infarction or angina
    OPCS-4 K40-K46, K49-K50, K75
    Note: this phenotype definition is broader than what is used in much published literature as it included stable angina in the case definition. The inventors have found that using a broad phenotype definition improves power for genetic association compared to a narrower phenotype.
    Note: in analyses using CAD as the outcome, Applicant excluded subjects who self-reported taking lipid lowering or blood pressure lowering medications.
  Hypertension (HTN)
    Applicant used medication-adjusted systolic blood pressure as a proxy for hypertension.
    Subjects who self-reported being on blood pressure medication had 15 mmHg added to their measured value.
    Blood pressure medications included ACE inhibitors, angiotensin II receptor blockers, calcium channel blockers,
  diuretics, alpha blockers, beta blockers, alpha-2 receptor agonists, central agonists, peripheral adrenergic inhibitors,
  and vasodilators.
  Venous thromboembolism (VTE)
    ICD-10 126, 180, 182.9, 022.3, 087.1; exclude controls with 174, 181-182, 022, 087, 088.2
    ICD-9 4151, 451, 453.9, 671.3, 671.4; exclude controls with 415.0, 444, 452-453, 593.81, 593.82, 671, 673.2
    Self-reported venous thromboembolic disease, pulmonary embolism, or deep vein thrombosis (1068, 1093, 1094);
  exclude controls with peripheral vascular disease or leg claudication (1067, 1087)

Atrial fibrillation (AFib)
  ICD-10 148; exclude controls with 147, 149
  ICD-9 427.3; exclude controls with 427
  Self-reported atrial fibrillation or flutter (1471, 1483); exclude controls with any other arrhythmia (1077, 1484, 1485, 1486, 1487)
  This phenotype includes atrial flutter. Applicant have found that using a broad AFib phenotype including atrial flutter improves power for genetic association compared to a narrower phenotype.
Chronic liver disease (CLD)
Applicant used alanine aminotransferase levels (ALT) as a proxy for CLD. ALT values greater than 84 U/L were set to 84 U/L, i.e. the phenotype was winsorized.
Type 2 diabetes (T2D)
  This phenotype excludes subjects with type 1 diabetes from both cases from controls, but allows cases with unspecified
diabetes with no T1D codes.
  ICD-10 E11, E14; exclude cases and controls with E10; exclude controls with E12-E13
  ICD-9 250
  Self-reported diabetes or type 2 diabetes (1220, 1223); exclude cases and controls with type 1 diabetes (1222); exclude
controls with gestational diabetes (1221)
  Doctor-diagnosed diabetes (UKB data field 2443)
  Any one of several self-reported medications, including metformin, PPARG agonists, sulfonylureas, non-sulfonylurea
secretagogues, and alpha-glucosidase inhibitors
Obesity (BMI)
  Body mass index was used as a proxy for obesity.
  For analyses using BMI, Applicant specifically focused on subjects who are obese (BMI>=30), as this is the most likely population who might be given a weight-loss drug. It appears that several pharmacomimetic variants have effects on BMI that are greatly amplified in obese subjects, even when expressed in relative terms (i.e. percent change in body weight). Applicant suspect this is due to gene x environment interactions.
Gout
  ICD-10 M10
  ICD-9 274
  Self-reported gout (1466)
Chronic kidney disease (CKD)
  Estimated glomerular filtration rate (eGFR) was used as a proxy for CKD.
  eGFR was estimated using the 2021 CKD-EPI(crea-cys) equation (Inker et al. 2021)
Age-related macular degeneration (AMD)
  ICD-10 H35.3; exclude controls with E10.3, E11.3, E12.3, E13.3, E14.3, H35, H36.0
  ICD-9 362.5; exclude controls with 362
  OPCS-4: exclude controls with C79-C85, X93
  Self-reported macular degeneration (1528); exclude controls with diabetic eye disease
Glaucoma
  ICD-10 H40, H42
  ICD-9 365
  OPCS-4 C60-C61, C65
  Self-reported glaucoma
  Any one of several glaucoma medications, including prostaglandin analogs and others (timolol, dorzolamide, brinzolamide, brimonidine tartrate, and levobunolol) For medications with both systemic and ocular uses, only eye drop formulations were used.

Alzheimer's disease (AD)

Due to the limited sample size of confirmed Alzheimer's disease cases in the UK Biobank, Applicant used a broad phenotype definition that included codes for "unspecified dementia".

ICD-10 G30, F00, F03; exclude controls with F01-F02, F04-F05, F06.7, G31, G32, R32, R41, R54

ICD-9 331.0; exclude controls with 290, 331

Exclude controls with self-report dementia or cognitive impairment (1263)

Alzheimer's disease (AD) (parental history score)

Applicant defined a score that combined observed AD in probands with self-reported parental history of AD, using the method of Janssen et al. 2019. The phenotype was defined as a count of affected parents, ranging from 0 to 2, with the value for probands with AD set to 2. Affected parents contribute 1 to the score. Unaffected parents contribute a fractional value reflecting the possibility that they will develop AD in the future, or would have if they had not died from another causes. The fractional value was computed as min(0.32, (100−current age or age at death, in years)/100). The 0.32 is an estimate of the maximum population prevalence of AD in people who survive to very old age.

Parkinson's disease

ICD-10: F02.3, G20; exclude controls with G21-G22

ICD-9: 332.0; exclude controls with 332.1

Self-reported Parkinson's disease (1262)

Parkinson's disease (parental history score)

This is constructed in the same manner as the AD parental history score described above, except with the fractional value for unaffected parents being set to min(0.029, (85−current age or age at death, in years)/85).

Migraine

ICD-10 G43; exclude controls with G44

ICD-9 346

Self-reported migraine

Migraine medication

Asthma

ICD-10 J45-46; exclude controls with J30, J33, L20

ICD-9 493; exclude controls with 471, 477, 691.80

OPCS-4: exclude controls with E08.1

Self-reported asthma (1111); exclude controls with allergic rhinitis, nasal polyps, or atopic dermatitis Nasal polyps ICD-10 J33; exclude controls with J30, J45, J46, L20

ICD-9 471; exclude controls with 477, 493, 691.80

OPCS-4 E08.1

Self-reported nasal polyps; exclude controls with asthma, allergic rhinitis, or atopic dermatitis Chronic obstructive pulmonary disease (COPD)

ICD-10 J41-J44; exclude controls with J40

ICD-9 491-492; exclude controls with 490

Self reported COPD, chronic bronchitis, or emphysema (1112, 1113, 1472); exclude controls with unspecified bronchitis Idiopathic pulmonary fibrosis (IPF)

ICD-10 J84.1; exclude controls with D86.0, D86.2, J60-J68, J70, J84.0, J84.2, J84.8, J84.9, J99, M05.1

ICD-9 516.3; exclude controls with 495, 500-506, 508, 515-517

Exclude controls with self-reported interstitial lung disease, asbestosis, pulmonary fibrosis, or fibrosing alveolitis (1115, 1120, 1121, 1122)

Osteoporosis

Applicant used heel bone mineral density (BMD) as a proxy for osteoporosis.

Osteoarthritis of Knee (OAofKnee)

ICD-10 M17; exclude controls with M05-M16, M18-M19, M25.5, M79.0

ICD-9 exclude controls with 712-716, 719.4, 729.0

Exclude controls with self-reported rheumatoid arthritis (1464), osteoarthritis (1465), gout (1466), "other joint disorder" (1467), psoriatic arthropathy (1477), joint pain (1537), or "arthritis (nos)" (1538).

Rheumatoid arthritis (RA)

ICD-10 M05-M06; exclude controls with M08.0

ICD-9 714.0-714.2

Self-reported rheumatoid arthritis (1464)

Crohn's disease (Crohn's)

Self-reported Crohn's disease (1462)

Exclude controls with ICD-10 K50 or ICD-9 555

Note: Applicant found that not including ICD codes in the case criteria greatly increased the consistency of Crohn's disease GWAS in UKB with published Crohn's disease GWAS from high-quality case-control cohorts. This might be related to the fact that the ICD-10 K50 code is called "Crohn's disease [regional enteritis]". Perhaps non-Crohn's enteritis cases are mistakenly being recorded using this code.

Ulcerative colitis (UC)

ICD-10 K51

ICD-9 556

Self-reported ulcerative colitis (1463)

Inflammatory bowel disease (IBD)

Union of Crohn's and UC phenotypes described above

Atopic dermatitis (AtoDerm)

ICD-10 L20; exclude controls with J30, J33, J45-J46

ICD-9 691.80; exclude controls with 471, 477, 493

OPCS-4: exclude controls with E08.1

Self reported eczema/dermatitis (1452); exclude controls with asthma, allergic rhinitis, or nasal polyps (1111, 1387, 1417)

Psoriasis

ICD-10 L40.0-L40.3, L40.8-L40.9; exclude controls with L40.4-L40.5

Self-reported psoriasis (1453)

Type 1 diabetes (T1D)

ICD-10 E10

Self-reported type 1 diabetes (1222)

Ankylosing spondylitis

ICD-10 M45; exclude controls with M46

ICD-9 720.0; exclude controls with 720

Self-reported ankylosing spondylitis (1313), exclude controls with self-reported "spine arthritis/spondylitis" (1311)

Celiac disease

ICD-10 K90.0

ICD-9 579.0

Exclude controls with self-reported "malabsorption/coeliac disease" (1456)

Multiple sclerosis (MS)

ICD-10 G35

ICD-9 340.9

Self-reported multiple sclerosis (1261)

Hypothyroidism
   ICD-10 E03
   ICD-9 243-244
   Self-reported hypothyroidism (1226)
   Self-reported levothyroxine prescription (1141191044)
Diverticulosis
   ICD-10 K57
   ICD-9 562
   Self-reported "diverticular disease/diverticulitis" (1458)
Uterine fibroids
   Exclude males from cases and controls
   ICD-10 D25-D26; exclude controls with C50-C58, D24, D27-D28, N93.8, N93.9, N94, N97, Z90.7
   ICD-9 218-219; exclude controls with 174, 179-184, 217, 220-221, 625, 626, 628
   OPCS-4 Q09.2; exclude controls with Q07-Q09, Y75.2
   OPCS-3 700.1; exclude controls with 691-698
   Self-reported uterine fibroids (1351); exclude controls with self-reported female infertility (1403), menor-rhagia (1556), or dysmenorrhea (1664)
Breast cancer
   ICD-10 C50
   ICD-9 174
   Self-reported breast cancer (1002)
Prostate cancer
   ICD-10 C61
   ICD-9 185
   Self-reported prostate cancer (1044)
Non-melanoma skin cancer
   ICD-10 C44; exclude controls with C43
   ICD-9 173; exclude controls with 172
   Self-reported non-melanoma skin cancer (1060), basal cell carcinoma (1061), or squamous cell carcinoma (1062); exclude controls with self-reported skin cancer (1003) or melanoma (1059)
Variant Selection
   For each disease, Applicant performed variant:PRS interaction tests using a set of variants that met all of the following criteria:
   The variant is associated either with the disease or a trait related to the disease at genome-wide significance ($p<5e-8$).
   The variant is associated with the disease at $p<5e-5$.
   If the variant is not associated with the disease at genome-wide significance, it must have been uniquely mapped to a gene using eQTL/pQTL colocalization analysis or fine-mapping of coding variants. For the QTL analyses, Applicant only used results from QTL datasets that Applicant deemed biologically
   relevant to the disease.
   If multiple independent variants meeting the selection criteria were mapped to the same gene for the same disease, Applicant only used the variant with the most significant association with the binary disease phenotype. For purposes of this filter, genome-wide significant variants that lacked a formal v2g mapping were mapped to the closest protein-coding gene.
   For computational convenience, at most 250 variants were tested per disease. If there were more variants meeting the above criteria, Applicant only tested the top 250 ranked by p-value of their association with the disease.
Computational Modeling
   For each (variant, disease) pair, Applicant fit a logistic regression model to predict the disease, or a linear regression model for diseases where Applicant use a biomarker as a proxy for the disease, e.g., BMI for obesity. In each model, the predictors were dosage of the variant, the PRS for the disease, an interaction term between the variant dosage and the PRS, and the following covariates: age, age squared, sex, genotyping chip, and PCs 1-6 of genetic ancestry.

A PRS in theory could include any particular variant being tested. Applicant did some experimentation and it seems this does not make a significant difference since each variant gives a small contribution to the overall PRS. But to be safe, prior to fitting the models, Applicant adjusted the PRS to control for the test variant's dosage. Specifically, Applicant fit a linear regression model PRS~test variant dosage and defined the controlled PRS as the original PRS minus the estimate from this model.

For quality control, Applicant conducted full GWAS for variant x PRS interactions for each disease phenotype. These are not exactly the model Applicant used for the main analysis, as they don't regress out each variant's effects from the PRS prior to association testing, but they are still informative with respect to whether the interaction tests are well-calibrated vs. whether they produce test statistics that are inflated. Looking at LD score regression intercepts (Bulik-Sullivan et al. 2015) for each GWAS, Applicant found that the test statistics had either no, minimal, or moderate inflation depending on the phenotype. Attenuation ratios for the GWAS that had inflated test statistics, i.e. (LDSC intercept−1)/(mean chi-squared statistic−1) (Loh et al. 2018), were usually greater than 0.5, indicating that the inflation was real and not an artifact of high statistical power in the GWAS (LD score regression intercepts scale with GWAS sample size and trait heritability, so small/negligible miscalibrations in the GWAS model can result in elevated intercepts for high-powered traits like BMI and height; but this was not the case for our GWAS).

To control our type I error (false positive) rates, Applicant therefore divided the chi-squared test statistics for each variant x PRS interaction test by the LD score regression intercept for the full variant x PRS interaction GWAS for the given disease phenotype.

Applicant then re-computed p-values from the adjusted test statistics. If the LD score regression intercept was less than 1, Applicant did not apply any correction.

Finally, to account for multiple testing, Applicant used a Bonferroni significance threshold of 0.05/the number of variants tested for a given disease. Applicant treats each disease analysis separately and does not correct for multiple testing across diseases.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A system for reducing memory processing resources, comprising:
    one or more processors configured by computer-readable instructions to:
        generate a plurality of principal components (PCs) and corresponding variant-PC loadings matrices from genetic variant data from a plurality of subjects with an identified human phenotype in a dataset to reduce a size of the dataset, wherein the genetic variants are an alteration, variant or polymorphism in a nucleic acid sample or genome of the subjects as compared to a reference genome,
            wherein the variant-PC loadings matrices are generated using values of variant effects for each phenotype based on external data of individuals;
        generate a biomarker stratifier score that is cumulative of data from across a plurality of biomarker stratifiers based at least on (i) one or more variant-PC loadings matrices, and (ii) biomarker stratifier weights for a human phenotype;
        determine, from the genetic variant data of human phenotypes, which genetic variants are pharmacomimetic instruments—that correspond to individual variants associated with the human phenotype based on statistical evidence;
        determine interactions between the pharmacomimetic instruments and the biomarker stratifier scores, wherein the interactions are indicative of a drug target-specific differential treatment response for the human phenotype; and
        perform one or more actions based on the determined interactions.

2. The system of claim 1, wherein the biomarker stratifier weights are PGS variant weights.

3. The system of claim 1, wherein the human phenotype is a disease of interest and the pharmacomimetic instruments used comprise sets of statistically independent variants that are disease-associated genetic variants.

4. The system of claim 3, wherein the pharmacomimetic instruments are disease-associated variants with an effect predictive of a drug's effect on a disease of interest.

5. The system of claim 4, wherein the instructions cause the one or more processors to generate an allelic score for the disease-associated variants of a disease of interest.

6. The system of claim 5, wherein disease-associated variants in the allelic score are weighted based at least on a second genome-wide association study.

7. The system of claim 1, wherein the dataset is based on genotyping arrays or whole-genome sequencing.

8. The system of claim 1, wherein the one or more processors are configured to determine the interactions between the pharmacomimetic instruments and the biomarker stratifier scores using a machine learning model.

9. The system of claim 1, wherein the plurality of PCs comprises at least 5 PCs.

10. The system of claim 1, wherein the plurality of subjects in the dataset comprise at least 200 subjects.

11. The system of claim 1, wherein each of the pharmacomimetic instruments satisfies a genome-wide significance threshold.

12. The system of claim 1, wherein the biomarker stratifier score for each entity is a scaled stratifier score.

13. The system of claim 12, wherein the scaled score is based at least on a raw polygenic score and a normalized polygenic score.

14. The system of claim 1, wherein the variant-PC loadings matrices are generated using values of variant effects for each phenotype in a matrix including rows each corresponding to a different variant and columns each corresponding to a different phenotype with values in cells formed from the rows and columns each indicating an effect of a variant of a row on a phenotype of a column intersecting with the row.

15. The system of claim 1, wherein the variant-PC loadings matrices are generated to include rows each corresponding to a different variant and columns each corresponding to a different principal component generated from the values of variant effects for each phenotype.

16. A method for reducing memory processing resources, comprising:
    generating a plurality of principal components (PCs) and corresponding variant-PC loadings matrices from genetic variant data from a plurality of subjects with an identified human phenotype in a dataset to reduce a size of the dataset, wherein the genetic variants are an alteration, variant or polymorphism in a nucleic acid sample or genome of the subjects as compared to a reference genome;
    generating a biomarker stratifier score that is cumulative of data from across a plurality of biomarker stratifiers based at least on (i) one or more variant-PC loadings matrices, and (ii) biomarker stratifier weights for a human phenotype,
        wherein the variant-PC loadings matrices are generated using values of variant effects for each phenotype based on external data of individuals;
    determining a set of disease-associated genetic variants which are pharmacomimetic instruments that correspond to the human phenotype based on statistical analysis;
    determining interactions between the pharmacomimetic instruments and the biomarker stratifier scores, wherein the interactions are indicative of a drug target-specific differential treatment response for the human phenotype; and performing one or more actions based on the determined interactions.

17. The method of claim 16, wherein the biomarker stratifier weights are PGS variant weights.

18. The method of claim 16, wherein the human phenotype is a disease of interest.

19. The method of claim 16, wherein the dataset is based on genotyping arrays or whole-genome sequencing to identify pharmacomimetic instruments that correspond to individual genetic variants associated with the human phenotype.

20. The method of claim 16, comprising determining the interactions between the pharmacomimetic instruments and the biomarker stratifier scores using a machine learning model.

\* \* \* \* \*